(12) United States Patent
Bao et al.

(10) Patent No.: US 11,517,689 B2
(45) Date of Patent: Dec. 6, 2022

(54) CONTROL FOR RESPIRATORY DEVICE

(71) Applicant: FISHER & PAYKEL HEALTHCARE LIMITED, Auckland (NZ)

(72) Inventors: Guohua Bao, Auckland (NZ); Venkata Subbarao Potharaju, Auckland (NZ); Arjen David Kat, Auckland (NZ); Gavin Andrew Bryson Ryan, Auckland (NZ); Ian Patrick Sarsfield Hickey, Auckland (NZ); Benjamin Wilson Casse, Auckland (NZ); Sujeewa Wannigama, Auckland (NZ); Gregory Martyn Smith, Auckland (NZ); Nordyn Alami, Auckland (NZ); Nimansha Budhiraja, Auckland (NZ); Donald Roy Kuriger, Auckland (NZ); Adam John Darby, Auckland (NZ); Bernhard Florian Lamprecht, Auckland (NZ); Jeremy Livingston Miller, Auckland (NZ); Johannes Nicolaas Bothma, Auckland (NZ); Dean Antony Barker, Auckland (NZ); Quinton Michael Smith, Auckland (NZ); Emma Louise Nasimi, Auckland (NZ); Andrew Jun Li, Auckland (NZ); Nicholas Edward Vaughan, Auckland (NZ); Zarin Kasad, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 690 days.

(21) Appl. No.: 14/909,622

(22) PCT Filed: Aug. 5, 2014

(86) PCT No.: PCT/NZ2014/000159
§ 371 (c)(1),
(2) Date: Feb. 2, 2016

(87) PCT Pub. No.: WO2015/020536
PCT Pub. Date: Feb. 12, 2015

(65) Prior Publication Data
US 2016/0193437 A1    Jul. 7, 2016

Related U.S. Application Data

(60) Provisional application No. 61/862,391, filed on Aug. 5, 2013.

(51) Int. Cl.
*A61M 16/00* (2006.01)
*A61M 16/16* (2006.01)
(Continued)

(52) U.S. Cl.
CPC ......... *A61M 16/0069* (2014.02); *A45C 3/001* (2013.01); *A61M 16/0003* (2014.02);
(Continued)

(58) Field of Classification Search
CPC .......... A61M 16/0069; A61M 16/0003; A61M 16/161; A61M 16/024; A61M 16/0051;
(Continued)

(56) References Cited

U.S. PATENT DOCUMENTS

| 6,046,676 A | * | 4/2000 | Ward ................ G06K 19/0723 340/572.1 |
| 6,050,260 A | * | 4/2000 | Daniell ............. A61M 16/1075 128/203.12 |

(Continued)

FOREIGN PATENT DOCUMENTS

| WO | WO 2006/053272 | 5/2006 |
| WO | WO 2012/080941 A1 | 6/2012 |
| WO | WO 2014/007655 | 1/2014 |

OTHER PUBLICATIONS

Written Opinion for PCT/NZ2014/000159 dated Dec. 16, 2014 in 8 pages.
(Continued)

*Primary Examiner* — Elliot S Ruddie
(74) *Attorney, Agent, or Firm* — Knobbe, Martens, Olson & Bear, LLP

(57) ABSTRACT

The operational parameters of a respiratory apparatus can be controlled through the use of a user interface located on a separate or separable mobile computing device. Sensors or features located on the mobile computing apparatus can be used to adjust the operation parameters or therapy of the
(Continued)

respiratory apparatus or otherwise improve the compliance of a patient utilizing the respiratory apparatus.

22 Claims, 12 Drawing Sheets

(51) Int. Cl.
| | |
|---|---|
| *G16H 40/63* | (2018.01) |
| *A45C 3/00* | (2006.01) |
| *G16H 20/40* | (2018.01) |
| *G16H 40/67* | (2018.01) |
| *A61M 16/10* | (2006.01) |
| *A61M 21/02* | (2006.01) |
| *A61M 21/00* | (2006.01) |
| *G06K 19/07* | (2006.01) |

(52) U.S. Cl.
CPC ...... *A61M 16/0051* (2013.01); *A61M 16/024* (2017.08); *A61M 16/1075* (2013.01); *A61M 16/16* (2013.01); *A61M 16/161* (2014.02); *G06K 19/0723* (2013.01); *G16H 20/40* (2018.01); *G16H 40/63* (2018.01); *G16H 40/67* (2018.01); *A45C 2003/002* (2013.01); *A61M 16/109* (2014.02); *A61M 16/1095* (2014.02); *A61M 21/02* (2013.01); *A61M 2016/0027* (2013.01); *A61M 2016/0033* (2013.01); *A61M 2021/0083* (2013.01); *A61M 2205/0205* (2013.01); *A61M 2205/18* (2013.01); *A61M 2205/273* (2013.01); *A61M 2205/332* (2013.01); *A61M 2205/3306* (2013.01); *A61M 2205/3334* (2013.01); *A61M 2205/3358* (2013.01); *A61M 2205/3368* (2013.01); *A61M 2205/3375* (2013.01); *A61M 2205/3553* (2013.01); *A61M 2205/3561* (2013.01); *A61M 2205/3569* (2013.01); *A61M 2205/3576* (2013.01); *A61M 2205/3584* (2013.01); *A61M 2205/3592* (2013.01); *A61M 2205/502* (2013.01); *A61M 2205/505* (2013.01); *A61M 2205/52* (2013.01); *A61M 2205/581* (2013.01); *A61M 2205/582* (2013.01); *A61M 2205/583* (2013.01); *A61M 2205/6018* (2013.01); *A61M 2205/6054* (2013.01); *A61M 2205/7527* (2013.01); *A61M 2205/8243* (2013.01); *A61M 2209/06* (2013.01); *A61M 2230/63* (2013.01)

(58) Field of Classification Search
CPC .............. A61M 16/1075; A61M 16/16; A61M 16/109; A61M 16/1095; A61M 21/02; A61M 2016/0027; A61M 2016/0083; A61M 2205/0205; A61M 2205/273; A61M 2205/3306; A61M 2205/332; A61M 2205/3334; A61M 2205/35; A61M 2205/3507; A61M 2205/3515; A61M 2205/3523; A61M 2205/3538; A61M 2205/3546; A61M 2205/3553; A61M 2205/3561; A61M 2205/3569; A61M 2205/3576; A61M 2205/3584; A61M 2205/3592; A61M 16/022; A61M 16/01; A61M 16/104; A61M 2016/103; A61M 2202/0208; A61M 2205/18; A61M 2205/6018; A61M 2230/205; A61M 2230/432; G16H 40/63; G16H 20/10; G16H 20/40; G16H 40/67; A45C 3/001; A45C 2003/002; G06F 19/00; G06F 19/3481; G06F 21/445; G06F 21/606; G06F 21/6245; G06K 7/10366–10405; G06K 7/10425; G06K 7/10465–10475; G06K 19/07; G06K 19/0723–0728; H04B 5/0031; H04L 67/12; H04L 2209/805; H04L 2209/88; H04L 9/3247; H04W 12/47

See application file for complete search history.

(56) References Cited

U.S. PATENT DOCUMENTS

| | | | |
|---|---|---|---|
| 6,591,834 B1* | 7/2003 | Colla | A61M 16/024 128/204.21 |
| 6,958,691 B1* | 10/2005 | Anderson | A61B 5/0002 340/539.12 |
| 7,610,094 B2 | 10/2009 | Stahmann et al. | |
| 2002/0020930 A1* | 2/2002 | Austin | A61M 16/16 261/119.1 |
| 2004/0016430 A1* | 1/2004 | Makinson | A61M 16/10 128/203.12 |
| 2006/0124128 A1* | 6/2006 | Deane | A61M 16/10 128/204.21 |
| 2007/0185739 A1* | 8/2007 | Ober | G16H 40/20 705/3 |
| 2007/0272239 A1* | 11/2007 | Aylsworth | A61M 16/1075 128/204.17 |
| 2008/0090595 A1* | 4/2008 | Liu | H04W 12/0806 455/461 |
| 2008/0110459 A1* | 5/2008 | Farbarik | A61M 16/0051 128/204.18 |
| 2009/0081951 A1* | 3/2009 | Erdmann | G16H 40/40 455/41.2 |
| 2010/0259388 A1* | 10/2010 | Menzel | G06Q 20/206 340/572.1 |
| 2011/0088693 A1* | 4/2011 | Somervell | A61M 16/1075 128/203.27 |
| 2011/0230779 A1* | 9/2011 | Titchener | A61B 5/087 600/538 |
| 2012/0167879 A1 | 7/2012 | Bowman et al. | |
| 2012/0192867 A1 | 8/2012 | Lewis et al. | |
| 2013/0239961 A1 | 9/2013 | Ross, Jr. et al. | |

OTHER PUBLICATIONS

International Search Report for PCT/NZ2014/000159 dated Dec. 16, 2014 in 3 pages.
Extended European Search Report for PCT/NZ2014/000159 dated Feb. 24, 2017 in 7 pages.
Office Action in corresponding European Patent Application No. 14834406.2, dated Jun. 15, 2018, in 5 pages.
Examination Report in corresponding Australian Patent Application No. 2014305232, dated Dec. 5, 2018, in 3 pages.
Extended Search Report in corresponding European Patent Application No. 20164315.2, dated Sep. 9, 2020, in 8 pages.

* cited by examiner

CONTROL FOR RESPIRATORY DEVICE

INCORPORATION BY REFERENCE TO ANY PRIORITY APPLICATIONS

This present application is a national phase of PCT Application No. PCT/NZ2014/000159, filed Aug. 5, 2014 titled "CONTROL FOR RESPIRATORY DEVICE," which claims priority to U.S. provisional patent application 61/862, 391, filed on 5 Aug. 2013, titled 'CONTROL FOR RESPIRATORY DEVICE', the disclosure of the specification of which is incorporated herein by reference.

BACKGROUND OF THE INVENTION

Field of the Invention

The present invention generally relates to controlling respiratory devices, such as respiratory devices for providing positive airway pressure therapy. More particularly, the present invention relates to the use of a mobile computing device to assist in the utilization and control of a positive airway pressure therapy apparatus.

Description of the Related Art

Respiratory disorders deal with the inability of a sufferer to effect a sufficient exchange of gases with the environment, leading to an imbalance of gases in the sufferer. These disorders can arise as a pathological consequence of an obstruction of the airway, insufficiency of the lungs in generating negative pressure, an irregularity in the nervous function of the brain stem, or some other disorder. Treatment of such disorders is diverse and depends on the particular respiratory disorder being targeted. In the first instance, a constriction of the airway, otherwise known as an obstructive apnea or a hypopnea (collectively referred to as obstructive sleep apnea or OSA), can occur when the muscles that normally keep the airway open in a patient relax during slumber to the extent that the airway is constrained or completely closed off, a phenomenon often manifesting itself in the form of snoring. When this occurs for a significant period of time, the patient's brain typically recognizes the threat of hypoxia and partially wakes the patient in order to open the airway so that normal breathing may resume. The patient may be unaware of these occurrences, which may occur as many as several hundred times per session of sleep. This partial awakening may significantly reduce the quality of the patient's sleep, over time potentially leading to a variety of symptoms, including chronic fatigue, elevated heart rate, elevated blood pressure, weight gain, headaches, irritability, depression, and anxiety.

Obstructive sleep apnea is commonly treated with the application of continuous positive airway pressure (CPAP) therapy. Continuous positive airway pressure therapy involves delivering a flow of gas to a patient at a therapeutic pressure above atmospheric pressure that will reduce the frequency and/or duration of apneas and/or hypopneas. This therapy is typically delivered by using a continuous positive airway pressure device (CPAP device) to propel a pressurized stream of air through a conduit to a patient through an interface or mask located on the face of the patient. The stream of air may be heated to near-body temperature. In some configurations, the stream of air may be humidified. In some such configurations, the stream of air may be humidified by forcing the stream of air to travel through a humidification chamber containing water and a heater for heating the water. In such configurations, the heater encourages the evaporation of the water, which in turn partially or fully saturates the stream of air with moisture. This moisture may help to ameliorate discomfort and/or mucosal tissue damage that may arise from the use of unhumidified CPAP therapy.

SUMMARY OF THE INVENTION

It is an object of the invention to provide an improved control system for controlling a respiratory device, or to at least provide the public with a useful choice.

A first aspect of the present invention provides a control system comprising:
a respiratory device; and
a mobile computing device configured to receive data from and/or transmit data to the respiratory device through at least one communications network, and comprising a user interface configured to control at least one operation parameter of the respiratory device.

In an embodiment, the mobile computing device is configured to, in response to receiving input from a patient or other user via the user interface, change the at least one operation parameter of the respiratory device.

In an embodiment, the user interface comprises at least one user interface element for conveying information to a patient or other user, and/or for receiving input from a patient or other user to control the at least one operation parameter of the respiratory device using the mobile computing device.

In an embodiment, the at least one user interface element comprises one or more of:
a blower element for a patient or other user to adjust the speed of, and/or turn on or off, a blower of the respiratory device;
a humidity setting element for a patient or other user to view or adjust a humidity setting of the respiratory device;
a wakefulness element for a patient or other user to turn on or off an operation of the mobile computing device and/or respiratory device that comprises changing the at least one operation parameter of the respiratory device in response to a change in a wakefulness of the patient;
a ramp element for a patient or other user to turn on or off an operation of the mobile computing device and/or respiratory device that comprises a ramping of a pressure and/or flow of gas propelled by the respiratory device, and/or for a patient or other user to change a ramp time of the respiratory device; and
a data element for a patient or other user to view information about the respiratory device, one or more operation parameters of the respiratory device, sensor data from one or more sensors, and/or information corresponding to sensor data from one or more sensors.

In an embodiment, the user interface comprises a graphical user interface.

In an embodiment, the mobile computing device is configured to communicate through the at least one communications network with, or comprises, at least one sensor, the at least one sensor comprising one or more of:
at least one environment sensor configured to generate data representing a condition of an environment about the mobile computing device and/or the respiratory device;
at least one patient sensor configured to generate data representing a condition of the patient; and
at least one respiratory device sensor configured to generate data representing an operating condition of the respiratory device.

In an embodiment, the at least one environment sensor comprises one or more of: a temperature sensor; a humidity sensor; an atmospheric pressure sensor; a light sensor; and a smoke sensor.

In an embodiment, the at least one patient sensor comprises one or more of: an accelerometer; an image sensor; and a sound sensor.

In an embodiment, the at least one respiratory device sensor comprises one or more sensors for generating data representing an operating condition of one or more of: a humidifier; a breathing conduit; a patient interface; and a blower.

In an embodiment, the mobile computing device is configured to perform at least one of the following:

present, via the user interface, information corresponding to data obtained from the at least one sensor to a patient or other user;

transmit a signal to automatically change, based on data generated by the at least one sensor, the at least one operation parameter of the respiratory device; and prompt, via the user interface, a patient or other user, based on data generated by the at least one sensor, to change the at least one operation parameter of the respiratory device.

In an embodiment, the mobile computing device is configured to, based on data generated by the at least one sensor, indicate an adverse operating condition of the respiratory device, and/or an adverse condition of an environment about the mobile computing device and/or the respiratory device, to a patient or other user.

In an embodiment, the mobile computing device is configured to determine a change in a wakefulness of a patient based on data obtained from the at least one sensor, and, in response to determining a change in wakefulness, to automatically perform at least one of the following:

transmit a signal to change the at least one operation parameter of the respiratory device;

transmit a signal to at least one other electrical device or appliance to change an operation parameter of the at least one other electrical device or appliance; and transmit a signal to a patient indicator device for waking the patient to trigger the patient indicator device.

In an embodiment, the at least one operation parameter of the respiratory device comprises one or more of: a treatment pressure; a treatment flow rate, a blower motor speed, a heater plate power and/or temperature, a heated breathing tube power, a humidification level, a time setting, an alarm setting, and a threshold for responding to a mask leak.

In an embodiment, the mobile computing device comprises at least one of: a laptop computer; a tablet computer; a personal digital assistant (PDA); a cellular phone; and a wearable computing device.

In an embodiment, the respiratory device comprises a continuous positive airway pressure (CPAP) device.

In an embodiment, the respiratory device comprises memory configured to store patient data corresponding to one or more patients and/or component data relating to one or more components of or for use with the respiratory device.

In an embodiment, the mobile computing device and/or another computing device are configured to transmit data to the respiratory device to update patient data and/or component data stored in memory of the respiratory device.

In an embodiment, the control system comprises:

at least one component of or for use with the respiratory device; and a wirelessly interrogatable chip integrated into or located on the at least one component, and having local memory configured to store information relating to the at least one component;

wherein the mobile computing device and/or another computing device are configured to wirelessly interrogate the chip to retrieve information about the at least one component; and the mobile computing device and/or other computing device are configured to transmit data corresponding to the retrieved information to the respiratory device to update component data stored in the memory of the respiratory device.

In an embodiment, the respiratory device comprises a near fields communications (NFC) chip having local memory configured to store patient data relating to one or more patients and/or component data relating to one or more components of or for use with the respiratory device; and the mobile computing device and/or another computer are configured to wirelessly transmit data to the NFC chip, through an NFC connection between the mobile computing device or other computer and the respiratory device, to update patient data and/or component data stored in the local memory of the NFC chip.

In an embodiment, the respiratory device does not have a user interface, such as a graphical user interface/display screen, for a patient or other user to manage therapy by controlling an operation of the respiratory device.

A further aspect of the present invention provides a method of controlling a respiratory device using a mobile computing device configured to receive data from and/or transmit data to the respiratory device through at least one communications network and comprising a user interface configured to control at least one operation parameter of the respiratory device, comprising:

controlling the at least one parameter of the respiratory device by transmitting a signal from the mobile computing device to the respiratory device through the at least one communications network.

In an embodiment, the method comprises the mobile computing device receiving input from a patient or other user via the user interface; and the mobile computing device, in response to receiving input from the patient or other user, changing the at least one operation parameter of the respiratory device by transmitting a signal to the respiratory device.

In an embodiment, the method comprises presenting to a patient or other user, via the user interface, at least one user interface element for conveying information to a patient or other user, and/or for receiving input from a patient or other user to control the at least one operation parameter of the respiratory device using the mobile computing device.

In an embodiment, the method comprises receiving input from a patient or other user via the at least one user interface element; and the mobile computing device, in response to receiving input from the patient or other user, performing one or more of the following:

adjusting the speed of, and/or turning on or off, a blower of the respiratory device;

adjusting a humidity setting of the respiratory device;

turning on or off an operation of the mobile computing device and/or respiratory device that comprises changing the at least one operation parameter of the respiratory device in response to a change in a wakefulness of the patient;

turning on or off an operation of the mobile computing device and/or respiratory device that comprises a ramping of a pressure and/or flow of gas propelled by the respiratory device, and/or changing a ramp time of the respiratory device; and presenting to a patient or other user, via the user interface, information about the respiratory device, one or more operation parameters of the respiratory device, sensor data from one or more sensors, and/or information corresponding to sensor data from one or more sensors.

In an embodiment, the user interface comprises a graphical user interface.

In an embodiment, the mobile computing device is configured to communicate through the at least one communications network with, and/or comprises, at least one sensor, and the method comprises one or more of:

the at least one sensor generating data representing a condition of an environment about the mobile computing device and/or the respiratory device;

the at least one sensor generating data representing a condition of the patient; and the at least one sensor generating data representing an operating condition of the respiratory device.

In an embodiment, generating data representing a condition of an environment about the mobile computing device and/or the respiratory device comprises one or more of:

generating data representing a temperature of an environment about the mobile computing device and/or the respiratory device;

generating data representing a humidity of an environment about the mobile computing device and/or the respiratory device;

generating data representing an atmospheric pressure of an environment about the mobile computing device and/or the respiratory device;

generating data representing the light in an environment about the mobile computing device and/or the respiratory device; and generating data representing the presence or absence of smoke in an environment about the mobile computing device and/or the respiratory device.

In an embodiment, generating data representing a condition of a patient comprises one or more of:

generating accelerometer data representing movement of a patient;

generating image data representing movement of a patient; and generating sound data representing sound emitted from a patient.

In an embodiment, generating data representing an operating condition of the respiratory device comprises:

generating data representing an operating condition of one or more of: a humidifier; a breathing conduit; a patient interface; and a blower.

In an embodiment, the method comprises the mobile computing device receiving data from the at least one sensor through the at least one communications network.

In an embodiment, the method comprises the mobile computing device performing at least one of the following:

presenting, via the user interface, information corresponding to data obtained from the at least one sensor to a patient or other user;

transmitting a signal to automatically change, based on data generated by the at least one sensor, at least one operation parameter of the respiratory device; and prompting, via the user interface, a patient or other user, based on data generated by the at least one sensor, to change at least one operation parameter of the respiratory device.

In an embodiment, the method comprises the mobile device, based on the data generated by the at least one sensor, indicating an adverse operating condition of the respiratory device, and/or an adverse condition of an environment about the mobile computing device and/or the respiratory device, to a patient or other user.

In an embodiment, the method comprises the mobile device determining a change in a wakefulness of a patient based on data generated by the at least one sensor, and, in response to determining a change in wakefulness, automatically performing one or more of:

transmitting a signal to change the at least one operation parameter of the respiratory device;

transmitting a signal to at least one other electrical device or appliance to change an operation parameter of the at least one other electrical device or appliance; and transmitting a signal to a patient indicator device for waking the patient to trigger the patient indicator device.

In an embodiment, the respiratory device comprises memory configured to store patient data relating to one or more patients and/or component data relating to one or more components of or for use with the respiratory device.

In an embodiment, the method comprises the mobile computing device and/or another computing device transmitting data to the respiratory device to update patient data and/or component data stored in memory of the respiratory device.

In an embodiment, the method comprises the mobile computing device or another computer wirelessly interrogating a chip to retrieve information relating to at least one component of or for use with the respiratory device, the chip being integrated into or located on the at least one component and having local memory configured to store information relating to the at least one component; and the mobile computing device or other computing device transmitting data corresponding to the retrieved information to the respiratory device to update component data stored in memory of the respiratory device.

In an embodiment, the respiratory device comprises a near fields communications (NFC) chip having local memory configured to store patient data relating to one or more patients and/or component data relating to one or more components of or for use with the respiratory device; and the method comprises:

the mobile computing device and/or another computer wirelessly transmitting data to the NFC chip, through an NFC connection between the mobile computing device or other computer and the respiratory device, to update patient data and/or component data stored in the local memory of the NFC chip.

In an embodiment, the at least one operation parameter of the respiratory device comprises one or more of: a treatment pressure; a treatment flow rate, a blower motor speed, a heater plate power and/or temperature, a heated breathing tube power, a humidification level, a time setting, an alarm setting, and a threshold for responding to a mask leak.

In an embodiment, the mobile computing device comprises at least one of: a laptop computer; a tablet computer; a personal digital assistant (PDA); a cellular phone; and a wearable computing device.

In an embodiment, the respiratory device comprises a continuous positive airway pressure (CPAP) device.

A further aspect of the present invention provides a computer readable medium on which is stored thereon computer-executable instructions, the computer-executable instructions being executable by a mobile computing apparatus to perform the methods described herein.

The term "comprising" as used in this specification and claims means 'consisting at least in part of'. When interpreting statements in this specification and claims which include the term "comprising", other features besides the features prefaced by this term in each statement can also be present. Related terms such as 'comprise' and 'comprised' are to be interpreted in a similar manner.

The phrase "respiratory device" as used in this specification and claims is intended to mean any device, system or apparatus that provides respiratory assistance to patients or users such as, but not limited to, those who require a supply of heated and humidified gases for respiratory therapies such as respiratory humidification therapy, high-flow oxygen therapy, Positive Airway Pressure (PAP) therapies, including CPAP therapy, Bi-PAP therapy, and OPAP therapy, and typically for the treatment of diseases such as Obstructive Sleep Apnea (OSA), snoring, or Chronic Obstructive Pulmonary Disease (COPD).

The term "computer-readable medium" should be taken to include a single medium or multiple media. Examples of multiple media include a centralised or distributed database and/or associated caches. These multiple media store the one or more sets of computer executable instructions. The term 'computer readable medium' should also be taken to include any medium that is capable of storing, encoding or carrying a set of instructions for execution by a processor of the mobile computing device and that cause the processor to perform any one or more of the methods described herein. The computer-readable medium is also capable of storing, encoding or carrying data structures used by or associated with these sets of instructions. The term 'computer-readable medium' includes solid-state memories, optical media and magnetic media.

The many hardware modules on a typical CPAP device, such as the sensors and the display screen on the user interface, are useful tools but increase the cost of producing such a device. Additionally the typical user interface on a typical CPAP device may feel esoteric to a patient, who may be more familiar with user interfaces found on consumer electronic devices containing microprocessors, including those found on laptop computers, tablet computers, personal digital assistants (PDAs), cellular phones (including those known as 'smart phones'), and computerized wristwatches (including those known as 'smart watches'). Accordingly, it is an object of the invention to present a solution to the above problems, or at least provide the public with a useful choice.

A mobile computing device, for example, a laptop computer, tablet computer, personal digital assistant (PDA), cellular phone, or computerized wristwatch, may be linked to a CPAP apparatus in such a way that the CPAP apparatus may be remotely controlled through use of a user interface located on the mobile computing device. Additionally, using the communication link, data obtained from sensors on or connected to the mobile computing device may be used to adjust various operating parameters of the CPAP device.

Additionally, several ways in which such mobile computing devices may interact with CPAP devices are disclosed.

Additionally, several ways in which such mobile computing devices may be used to help the patient comply with a CPAP therapy regime or otherwise make managing therapy more convenient for the patient are disclosed.

In the description in this specification reference may be made to subject matter which is not within the scope of the appended claims. That subject matter should be readily identifiable by a person skilled in the art and may assist in putting into practice the invention as defined in the presently appended claims.

BRIEF DESCRIPTION OF THE DRAWINGS

The above and other features, aspects and advantages of the present invention will be described, by way of non-limiting example only, with reference to the following figures.

DETAILED DESCRIPTION OF THE PREFERRED EMBODIMENT

Overview

The hardware modules of a CPAP apparatus, including sensors and user interfaces, are useful in managing therapy and providing controllability for the user, but increase the cost of producing such an apparatus. The sensors of a CPAP apparatus may include, for example but without limitation, temperature, humidity and pressure sensors. Relatively inexpensive mobile computing devices, including products such as, for example but without limitation, laptop computers, tablet computers, personal digital assistants (PDAs), cellular phones, wearable computing devices including head-mounted computing devices (e.g. computerized glasses) and computerized wristwatches, and implantable computing devices, have become readily available in the consumer electronics market. Additionally, it has become common for mobile computing device manufacturers, particularly cellular phone manufacturers, to include various sensors in the devices. For example, Samsung currently markets the Galaxy S™4, which includes a barometer, thermometer, hygrometer, accelerometer, microphone, and image/motion sensor, along with Global Positioning System (GPS) utilization capability (as seen on the following website: http://www.samsung.com/global/microsite/galaxys4/, accessed 29 Jul. 2013). It may be advantageous to delegate some of the features of the CPAP apparatus to the mobile computing device, and have the mobile computing device communicate with the CPAP apparatus to reduce the cost of producing the CPAP apparatus and improve the convenience of use of the CPAP apparatus.

Figure 1:
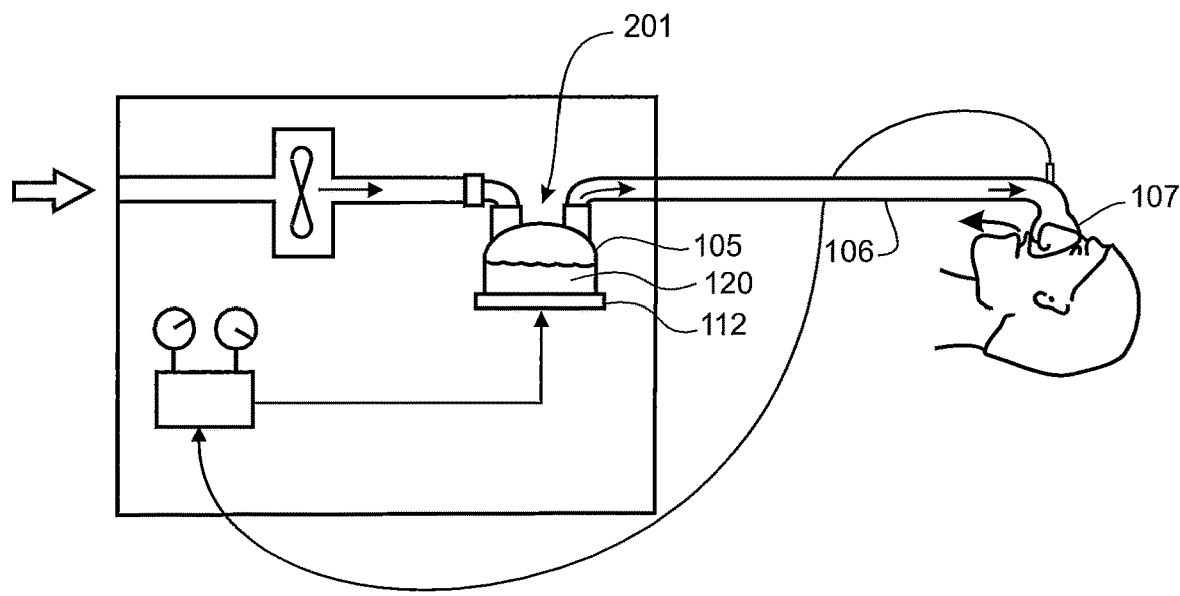
FIG. 1 is a graphical depiction of a positive airway pressure apparatus.
Figure 2:
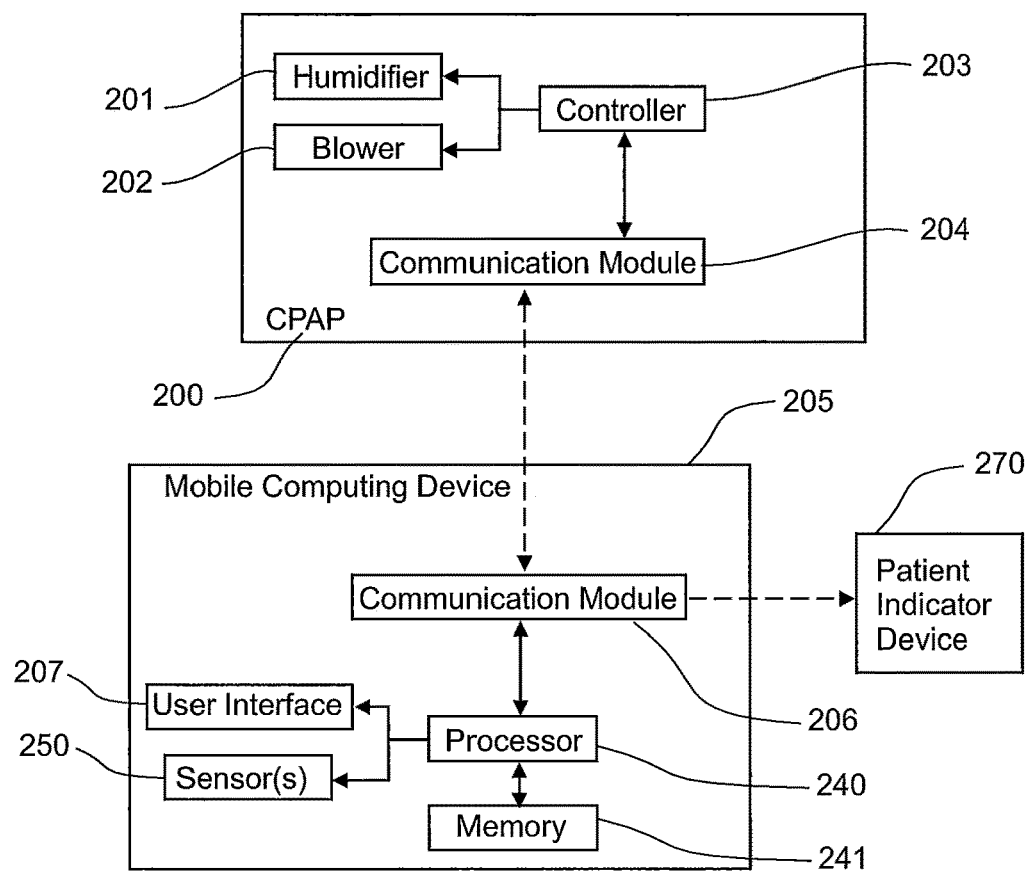
FIG. 2 is a block diagram showing the components facilitating the interaction of a mobile computing device and a positive airway pressure apparatus.

FIG. 2 is a block diagram illustrating an embodiment of a CPAP device/apparatus 200 incorporating certain features, aspects and advantages of an embodiment of the present invention. The CPAP apparatus 200 comprises a blower 202 that propels a stream of pressurized air through a breathing conduit 106 (see FIG. 1) to an interface 107 wearable by a patient. The CPAP apparatus 200 also preferably comprises a humidifier 201, which may be used to humidify air passing through it. The humidifier 201 is preferably a pass over type humidifier where air passing through the humidifier 201 picks up a quantity of water vapour from a reservoir 105 containing a supply of water 120. The water reservoir 105 may be heated by a heater 112. The humidifier 201 preferably is integrated into the housing of the CPAP apparatus 200. In some configurations, the humidifier 201 may be a separate component within the housing of the CPAP apparatus 200 or separate from the CPAP apparatus 200 with a conduit connecting the CPAP apparatus 200 and the humidifier 201. Other types of humidifiers, other than a pass over type, such as passive heat and moisture exchangers (HMEs), for example but without limitation, may be used. Additionally, in some configurations, multiple humidifiers may be used with the CPAP apparatus 200.

The blower 202 and/or the humidifier 201 may be controlled by a controller 203, which preferably comprises a microprocessor with associated memory or some other suitable control configuration. The controller 203 may interact with a communication module 204, which may transmit and/or receive control signals and/or other data to and/or from a corresponding communication module 206 in a mobile computing device 205 through at least one communication or data link, such as at least one communications network. The at least one communications network may be any suitable wired or wireless communications network or combination of wired communications network(s) and/or wireless communications network(s). In some configurations, the communication modules 204, 206 can be radiofrequency (RF) modules capable of communication. In some configurations, the modules 204, 205 can communicate through one or more types of wireless networks and associated protocols, including but not limited to WiFi, Bluetooth, and 2G/3G/4G. In some configurations, the communication modules 204, 206 may communicate using a wired connection, such as a data transmission wire, for example but without limitation. In some configurations, the communication modules 204, 206 may communicate via a USB, Ethernet, FireWire or serial port interface, for example but without limitation. In some configurations, the mobile communication device 205 may directly dock to at least a portion of the CPAP apparatus 200.

The mobile communication device 205 comprises a processor 240 with associated memory 241 configured to execute computer-executable instructions, one or more sensors 250 configured to generate sensor data and preferably a user interface 207 that comprises one or more display screens, buttons, levers, touch screens, and/or other input elements/peripherals that may be used to help a patient control the CPAP apparatus 200.

Figure 5:
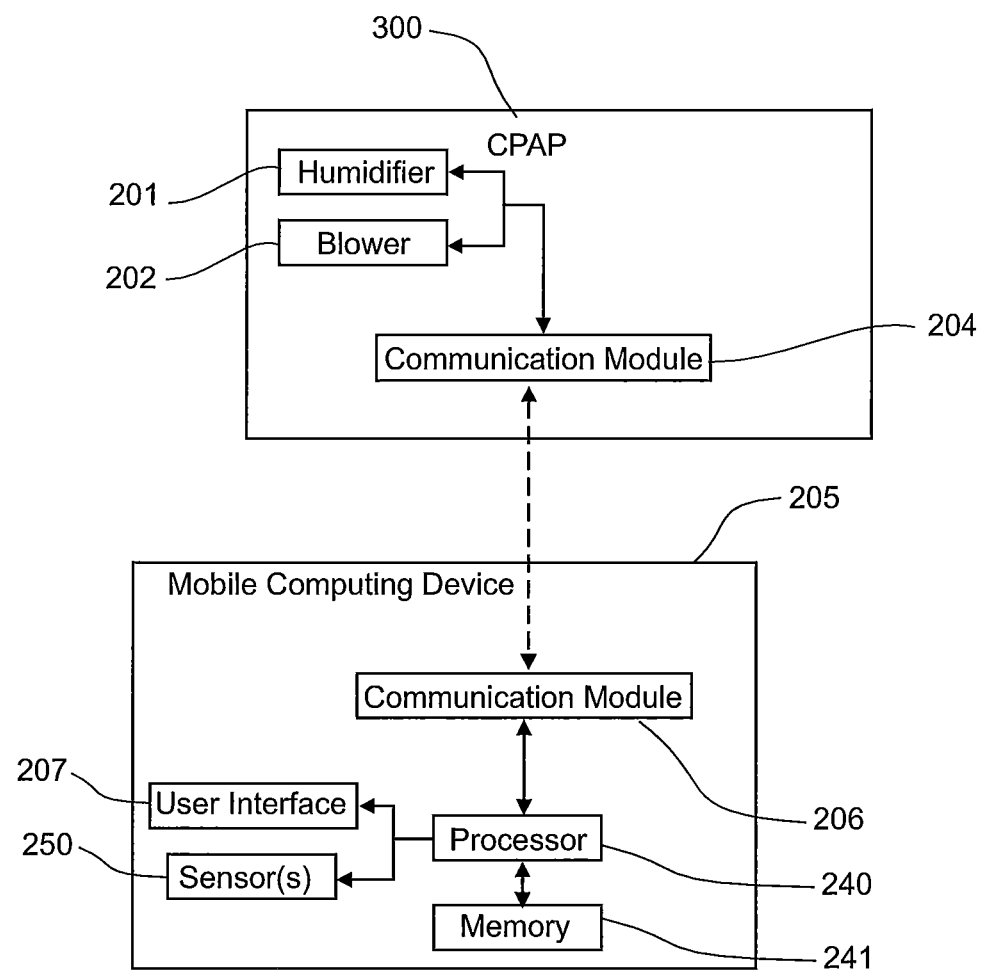
FIG. 5 is a block diagram showing the components facilitating the interaction of the mobile computing device of FIG. 2 and an alternative positive airway pressure apparatus.

FIG. 5 is a block diagram illustrating one alternative CPAP apparatus 300. The CPAP apparatus 300 is substantially the same as the CPAP apparatus 200 shown in FIG. 2, except the CPAP apparatus 300 does not have a separate controller (such as the controller 203) for controlling the operation of the CPAP apparatus such as processing sleep algorithm and controlling the blower and/or humidifier. In some configurations, the mobile computing device 205 may instead be configured to control via control signals the CPAP apparatus 300, including the blower 202 and/or the humidifier 201, by processing sleep algorithms, for example, at the mobile computing device 205 using sensor data and patient settings (rather than a controller of the CPAP apparatus processing the sleep algorithms). In some configurations, the mobile computing device 205 may be configured to enable cloud-based processing of sleep algorithms, for example, and control of the CPAP apparatus through the mobile computing device 205.

Various Embodiments

Various ways in which the mobile computing device 205 may advantageously interact with the CPAP apparatus 200 include but are not limited to those are listed below:

The mobile computing device 205 may adjust the operation parameters of the CPAP apparatus 200 through one or more graphical user interface(s) located on one or more display screen(s) of the mobile computing device 205. The screen(s) could be any suitable screen(s), such as an (optionally colour) LED or LED screen(s). The graphical user interface(s) may comprise text and/or one or more icons, graphics, boxes, tabs, or other elements that may be used to present/convey information to the patient.

The graphical user interface may be loaded manually by the patient prior to use with the CPAP apparatus 200. In some configurations, the graphical user interface may automatically load, pop-up and/or launch upon sensing a nearby CPAP apparatus 200 capable of communication with the mobile computing device 205. In some configurations, the graphical user interface may load, pop-up and/or launch upon pairing, docking or connection of the mobile computing device 205 and the CPAP apparatus 200.

The operation parameters of the CPAP apparatus 200 that are capable of being adjusted may include, but are not limited to, treatment pressure, flow, motor speed, heater plate power/temperature, heated breathing tube power, level of humidification, clock/time settings, alarm clock settings, and thresholds for responding to mask leaks. Additionally, such parameters along with other data, including data obtained by sensors on, within or connected to the CPAP apparatus 200 can be displayed on the display screen of the mobile computing device 205. Other data concerning the CPAP apparatus 200, including the product family, the model number, the serial number, and/or the software version, for example but without limitation, may be obtained from the CPAP apparatus 200 and/or the internet and displayed on the display screen of the mobile computing device 205. The graphical user interface on the display screen may be controlled with input from a patient through the use of one or more interface elements of the user interface presented to the patient. Patient input may be via tactile or non-tactile buttons, levers, keyboards, touch pads, and/or other peripherals associated with the mobile computing device 205, for example. In some configurations, the graphical user interface on the display screen may be controlled through voice commands that can be recognized through the use of software installed on the mobile computing device 205. In this manner, it is possible to construct a CPAP apparatus 200 with little or no user interface by delegating the features of the user interface to the mobile computing device 205.

Figure 4A:
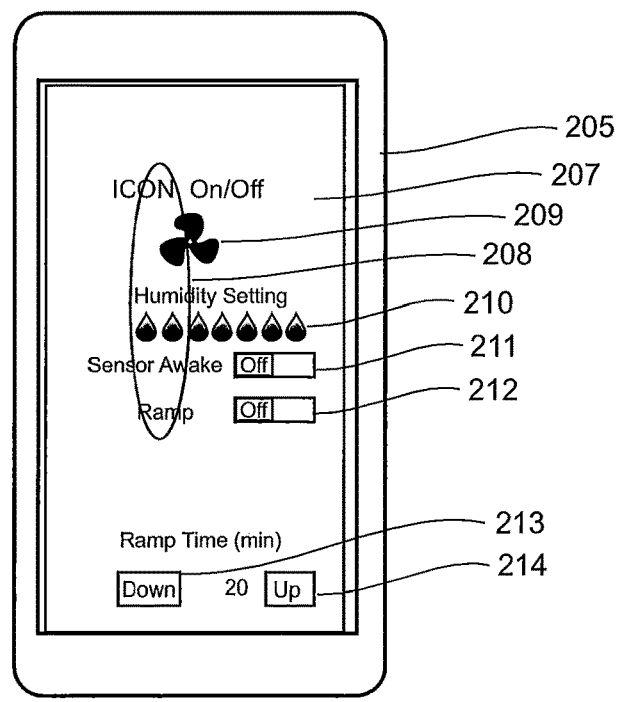
FIG. 4A is a graphical depiction of a mobile computing device comprising a graphical user interface capable of interacting with a positive airway pressure apparatus.
Figure 4B:
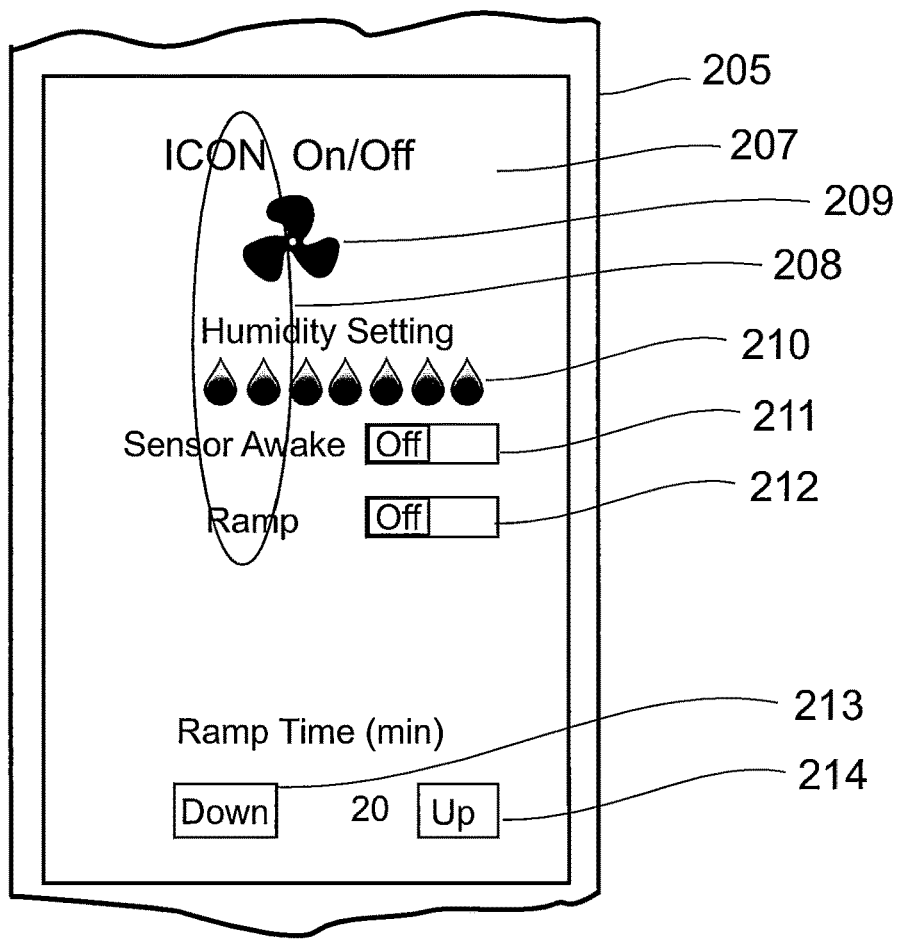
FIG. 4B is another graphical depiction of a mobile computing device comprising a graphical user interface capable of interacting with a positive airway pressure apparatus.

FIGS. 4A and 4B are graphical depictions of an embodiment of the graphical user interface on the mobile computing device 205. In the illustrated configuration, the mobile computing device 205 is shown in the form of a cellular phone comprising a display screen 207 comprising a graphical user interface 208. The display screen 207 also can function as a touch-sensitive pad for interacting with the graphical user interface 208. The graphical user interface 208 may include interface elements such as, for example but without limitation, a CPAP blower on/off button 209, a changeable humidity setting 210, a 'Sensor Awake' on/off setting 211, a ramp on/off setting 212, and buttons 213, 214 for decreasing and increasing the ramp time, respectively. The 'Sensor Awake' on/off setting refers to a wakefulness element or module for turning on/off an operation of the mobile computing device 205 and/or the CPAP apparatus 200 (such as by using the SensAwake™ control algorithm developed by Fisher and Paykel Healthcare) that comprises detecting the wakefulness of the patient and modulating one or more operation parameters of the CPAP apparatus 200, such as the pressure of therapy, based on the wakefulness of the patient. The graphical user interface 208 may also comprise a 'data' button (not pictured) that, when pressed, may display, though the use of one or more pop-up window(s) or some other display configuration, one or more value(s) conveying information to the patient. This information may convey at least one or more of the following: compliance data, therapy efficacy data, trending data representing compliance and/or therapy efficacy for a patient over time, AHI data, number of hours used, severity of mask leak, current humidity, current pressure, current flow, and/or data concerning the CPAP apparatus (including but not limited to, the product family, model number, serial number, and/or software version). Thus, the given graphical user interface 208 on the mobile computing device 205 may help the patient change operation parameters of the CPAP apparatus and/or access data.

Figure 3:
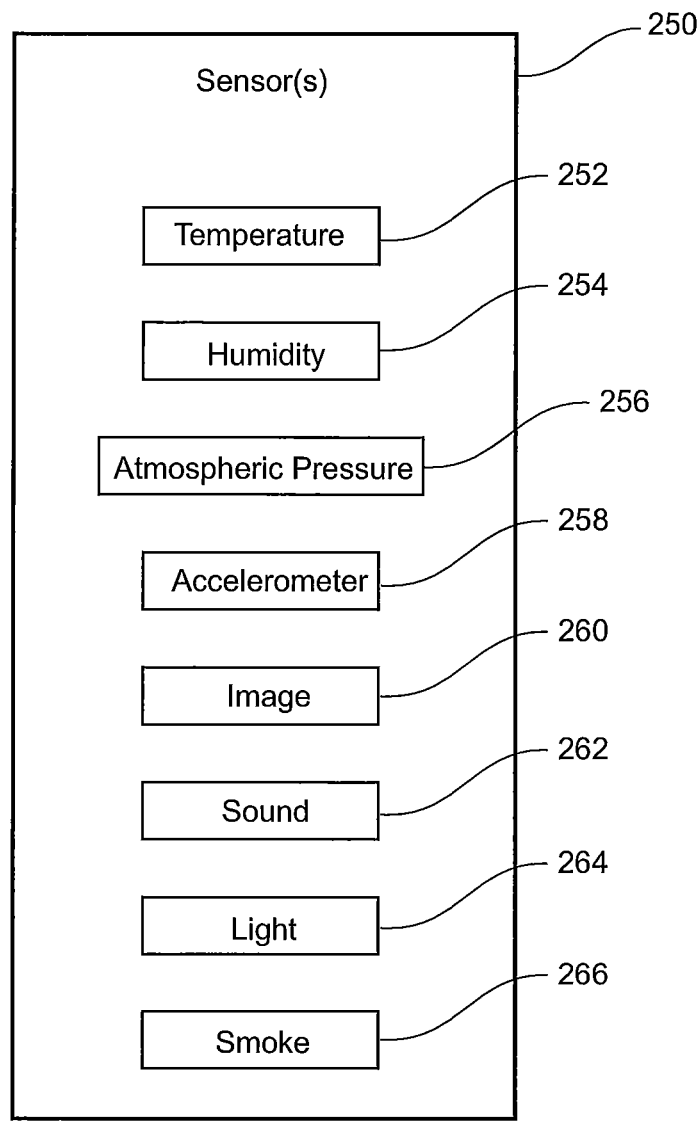
FIG. 3 is a simplified block diagram showing sensors of the mobile computing device.

The mobile computing device 205 may use any sensors 250 (see FIG. 3) that might be available on the mobile computing device 205, and/or any sensors that might be available on the CPAP apparatus 200, to assist in the control of the CPAP apparatus 200 or otherwise help the patient in selecting parameters for the CPAP apparatus 200. In some configurations, such sensors may be configured to determine, for example, a condition of the environment around the CPAP apparatus 200 and/or the mobile computing device 205, and/or to determine a condition of the patient. In some configurations, such sensors may comprise one or more of a temperature sensor 252, a humidity sensor 254, an atmospheric pressure sensor 256, an accelerometer 258, an image (e.g. camera) sensor 260, a sound (e.g. microphone) sensor 262, and a light sensor 264. Some possible uses for such sensors include but are not limited to any that are listed below:

A temperature sensor 252, if present on the mobile computing device 205, may be used to determine the temperature of the environment around the CPAP apparatus 200 and the patient if the mobile computing device 205 is placed in the same general area (for example, the same room) as the patient and/or the CPAP apparatus 200. In some configurations, the mobile computing device 205 may use this data to, for example, automatically adjust the power/temperature applied to the heater plate 112 of the humidifier 201 (e.g., if the humidifier 201 is one that contains a heater plate 112) and/or heated breathing tubes/conduits 106 in response to one or more temperatures detected during a therapy session. In some configurations, the mobile computing device 205 may use this data to suggest to/prompt a patient or other user to change the power/temperature applied to the heater plate 112 and/or heated breathing tubes/conduits 106 in response to one or more temperatures detected during a therapy session. Thus the temperature sensor 252 can be used to help in delivering the respiratory gases at the temperature most suitable for or desired by the patient.

A humidity sensor 254, if present on the mobile computing device 205, may be used to determine the humidity of the environment around the CPAP apparatus 200 and the patient if the mobile computing device is placed in the same general area (for example, the same room) as the patient and/or the CPAP apparatus 200. In some configurations, the mobile computing device 205 may use this data to, for example, automatically adjust the power/temperature applied to the heater plate 112 of the humidifier 201 (e.g., if the humidifier 201 is one that contains a heater plate 112) and/or heated breathing tubes/conduits 106 in response to one or more humidity readings obtained over the course of a therapy session. In some configurations, the mobile computing device 205 may use this data to suggest to/prompt a patient or other user to change the power/temperature applied to the heater plate 112 and/or heated breathing tubes/conduits 106 in response to one or more humidity readings obtained over the course of a therapy session. Thus, the humidity sensor 254 can be used to help in delivering the respiratory gases at the humidity most suitable for or desired by the patient, while helping to reduce or eliminate rain-out within the breathing tubes/conduits 106 and/or patient interface (e.g. mask) 107.

An atmospheric pressure sensor/barometer 256, if present on the mobile computing device 205, may be used to determine the atmospheric pressure of the environment around the CPAP apparatus 200 and the patient if the mobile computing device is placed in the same general area (for example, the same room) as the patient and/or the CPAP apparatus 200. The atmospheric pressure detected by the sensor 256 could change relative to the altitude at which the detection takes place. Additionally, the CPAP apparatus 200 may require higher or lower fan speeds or valve settings depending on the atmospheric pressure at which the CPAP apparatus 200 is used. Thus, the mobile computing device 205 may use this atmospheric pressure data to, for example, automatically adjust the pressure and/or flow settings of the CPAP apparatus 200, and/or the power/temperature applied to the heater plate 112 of the humidifier 201 (e.g., if the humidifier 201 is one that contains a heater plate 112) and/or heated breathing tubes/conduits 106, in response to one or more pressures detected during a therapy session. In some configurations, the mobile computing device 205 may use this data to suggest to/prompt a patient or other user to change the pressure and/or flow settings of the CPAP device 200, the power/temperature applied to the heater plate 112 and/or heated breathing tubes/conduits 106, in response to one or more pressures detected during a therapy session. Thus, the barometer 256 can be used to help in delivering the respiratory gases at the desired pressure and/or flow rate at a given altitude, which, for example, may be different to the altitude the patient normally uses the CPAP apparatus 200 due to travel.

An accelerometer 258, if present on the mobile computing device 205, may be used to monitor the patient's movements during a CPAP therapy session. Movement of the body may occur when the patient is suffering from an obstructive sleep apnea episode treatable by an adjustment of pressure and/or flow of gases in the CPAP apparatus 200. By placing the mobile computing device 205 onto the bed, near the patient (e.g. in the patient's pocket, etc), or on the patient (e.g. attachment to the skin through use of an adhesive pad, etc), the mobile computing device may use the accelerometer 258 to track the patient's movement during the CPAP therapy session, and may use this movement data to automatically adjust said the pressure and/or flow settings of the CPAP device 200 in response to one or more movements detected in a therapy session. Alternatively or in addition to the above, the patient's movements may indicate a transition from a relatively heavy sleep state to a relatively light sleep state. The mobile computing device 205 may use such motions to determine the wakefulness of the patient and alter the pressure and/or flow of gases in the CPAP apparatus 200 based on such a determination of wakefulness. For example, if the motions sensed by the accelerometer 258 in the mobile computing device 205 indicate that the patient is waking, this may trigger a decrease in the pressure and/or flow of the gases in the CPAP apparatus 200, which may be more tolerable for the patient.

A visual sensor, such as an image sensor/camera 260, if present on the mobile computing device 205, may be used to monitor the patient's movements during a CPAP therapy session. Movement of the face, neck, and/or body may occur when the patient is suffering from an obstructive sleep apnea episode treatable by an adjustment of pressure and/or flow of gases in the CPAP apparatus 200. By focusing the image sensor/camera 260 of the mobile computing device 205 onto a patient (or directing the image sensor/camera 260 toward the patient), it may be possible to analyze image data acquired for evidence of the apnea episodes, and to use such image data indicating the presence of the sleep apnea episodes to help in adjusting the pressure and/or flow settings of the CPAP apparatus 200. In some configurations, the image sensor/camera 260 may be used to detect gestures or signs of the patient, which in turn could be used as a form of input for changing operation parameters of the CPAP apparatus 200.

A sound sensor 262, if present on the mobile computing device 205, may be used to measure the sound coming from a patient during a CPAP therapy session. Sounds, such as those occurring during a snoring episode or during exhalation or inhalation of gases through a normal or constrained airway, may be used to help in the diagnosis of an obstructive sleep apnea episode treatable by an adjustment of pressure and/or flow of gases in the CPAP apparatus 200. By focusing or directing the sound sensor 260 of the mobile computing device 205 onto a patient, it may be possible to analyze acoustic data acquired for evidence of the sleep apnea episodes, and to use such acoustic data indicating the presence of the sleep apnea episodes to help in adjusting the pressure and/or flow settings of the CPAP apparatus 200. In some configurations, the sound sensor 260 may be used to detect voice or other audible commands by the patient, which in turn could be used as a form of input for changing operation parameters of the CPAP apparatus 200.

A light sensor 264, if present on the mobile computing device 205, may determine the presence or absence of light in the environment around the CPAP apparatus 200 and the patient if the mobile computing device 205 is placed in the same general area (for example, the same room) as the patient and/or CPAP apparatus 200. It may be that the patient or another person may wish to turn off or dim a light, such as light in the same room as the patient for example, when the patient intends to sleep. Likewise, it may be that the patient or another person may wish to turn on or brighten a light, such as light in the same room as the patient for example, when the patient intends or needs to become more awake. In this embodiment, a sudden or gradual decrease in the amount of light in the surrounding environment may be sensed by the light sensor 264 on the mobile computing device 205, which may in response prompt the CPAP apparatus 200 to increase or ramp up the pressure and/or flow. Similarly, a sudden or gradual increase in the amount of light in the aforementioned environment may be sensed by the light sensor 264 on the mobile computing device 205, which may in response prompt the CPAP apparatus 200 to decrease or ramp down the pressure and/or flow. In one embodiment, a light sensor 264, if present on the mobile computing device may be used to control the brightness of a display of the CPAP apparatus 200, if a display is present on the CPAP apparatus 200. If the mobile computing device 205 determines that the light is relatively bright in the environment around the CPAP apparatus 200, for example, the mobile computing device 205 may automatically decrease the brightness of and/or turn off a backlight of the display, if the display has a backlight. Alternatively, if the mobile computing device 205 determines the light is relatively dark in the environment surrounding the CPAP apparatus 200, for example, the mobile computing device 205 may automatically increase the brightness of and/or turn on the backlight.

In one embodiment, the CPAP apparatus 200 may comprise a display and at least one light sensor for determining the presence or absence of light in the environment around the CPAP apparatus 200. The light sensor may be integrated with the housing of the CPAP apparatus 200. Alternatively, the light sensor may be separate from the CPAP apparatus 200, for example, and configured to communicate with the CPAP apparatus 200 through a wireless or wired data connection. The CPAP apparatus 200 may be configured to use the data from the light sensor to adjust the brightness of the display of the CPAP apparatus 200 in responses to a change in the amount of light in the surrounding environment, as mentioned above in paragraph [0091].

In one embodiment, the mobile computing device 205 and/or the CPAP apparatus 200 may comprise a smoke sensor 266 for determining the presence or absence smoke in the environment around the CPAP apparatus 200. The smoke could be due to a failure in the CPAP apparatus 200 for example, or from outside the CPAP apparatus 200. In one embodiment, the smoke sensor 266 may be integrated into the housing of the CPAP apparatus 200. For example, the smoke sensor 266 may be integrated into an air circuit of the CPAP apparatus 200. Alternatively, the smoke sensor 264 may be separate from the mobile computing device 205 and/or the CPAP apparatus 200, and configured to communicate with the CPAP apparatus 200 and/or the mobile computing device 205 through a wireless or wired data connection. If smoke is detected, the CPAP apparatus 200 and/or the mobile computing device 205 may shut down the CPAP apparatus 200. The CPAP apparatus 200 and/or the mobile computing device 205 may also activate an alarm to make a patient or other user aware of the smoke condition. The alarm may be an audio, visual and/or tactile indicator, for example.

In some configurations, one or more of the sensors useful in managing therapy and/or providing controllability for the user (e.g temperature, humidity, atmospheric pressure, accelerometer, image/camera, sound, light and/or smoke sensors, if present) may be sensors that are separate from/external to both the CPAP apparatus 200 and the mobile computing device 205. For example, a humidity sensor that is separate to both the CPAP apparatus 200 and the mobile computing device 205 may be used to determine the humidity of the environment around a patient, the CPAP apparatus 200 and/or the mobile computing device 205. The humidity sensor may be a relative humidity sensor. The humidity sensor may communicate with the CPAP apparatus 200 and/or the mobile computing device 205 through a wireless or wired data connection. It will be understood that the wireless or wired data connection may include any direct or indirect connection for the communication of data and may include a combination of wireless and/or wired data connections. Further, there may be intervening elements between the connected integers. In some configurations, the humidity sensor may communicate with the CPAP apparatus 200 through a USB or Secure Digital Input Output (SDIO) card interface, for example but without limitation. The housing of the CPAP apparatus 200 may comprise one or more USB ports for example, and the humidity sensor may comprise a housing and plug that can be plugged directly into one of the port(s). In some configurations, connecting the humidity sensor to the CPAP apparatus 200 and/or the mobile computing device 205 may enable and/or activate a humidity-controlling functionality of the CPAP apparatus 200 and/or the mobile computing device 205 using humidity data from the humidity sensor. Similarly, connecting other sensors (such as temperature, atmospheric pressure, accelerometer, image/camera, sound, light and/or smoke sensors, if present) that are separate from/external to both the CPAP apparatus 200 and the mobile computing device 205, and/or components of or for use with the CPAP apparatus 200, may enable and/or activate a corresponding functionality of the CPAP apparatus 200 and/or the mobile computing device 205.

Figure 6:
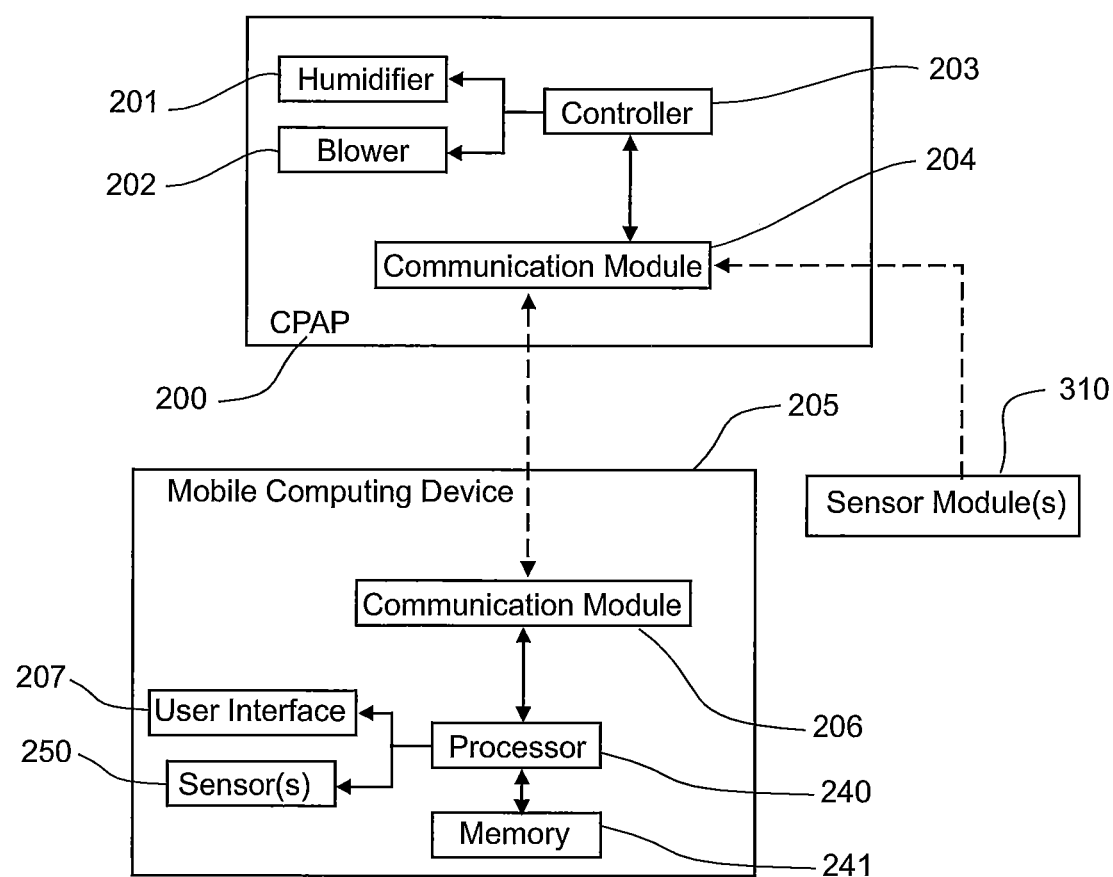
FIG. 6 is a block diagram showing the mobile computing device and the positive airway pressure apparatus of FIG. 2, and a sensor module configured to communicate with the positive airway pressure apparatus.
Figure 7:
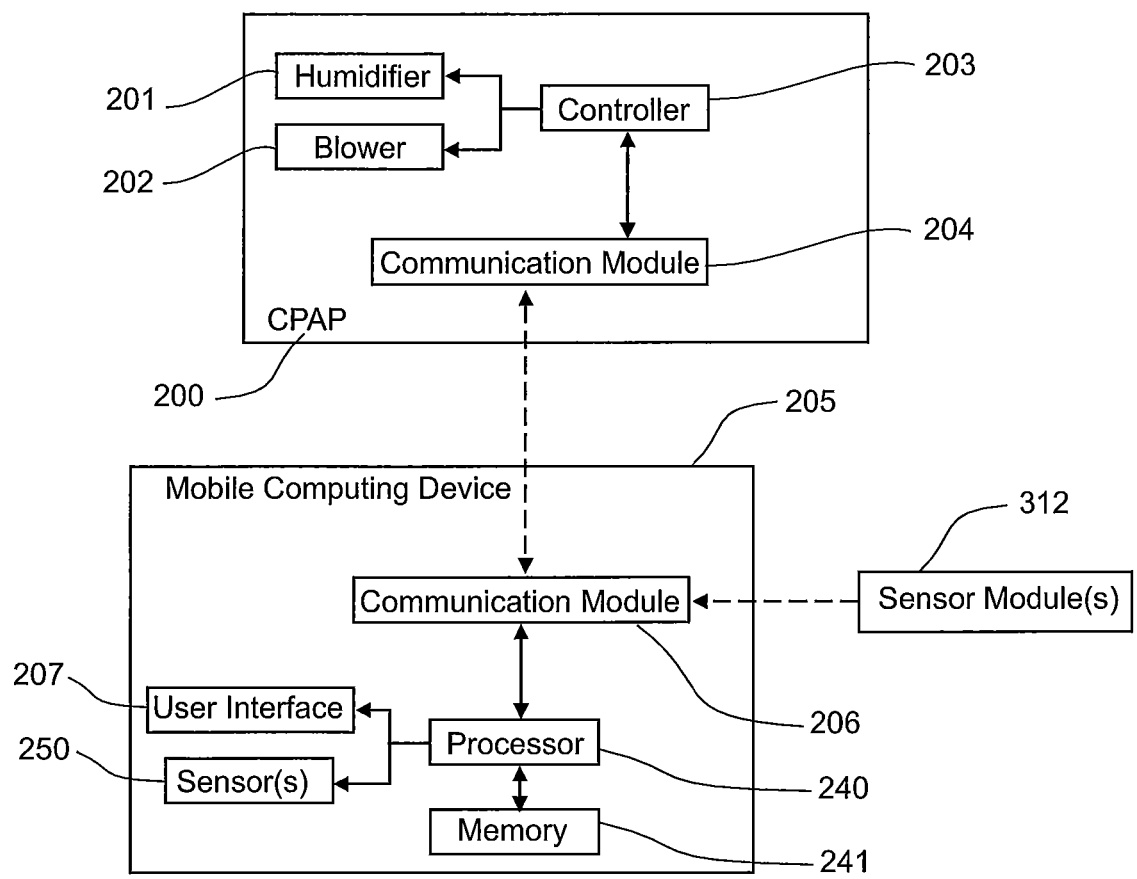
FIG. 7 is a block diagram showing the mobile computing device and the positive airway pressure apparatus of FIG. 2, and a sensor module configured to communicate with the mobile computing device.

In some configurations, with reference to FIGS. 6 and 7, at least one sensor module 310, 312 having one or more of sensors useful in managing therapy and/or providing controllability for the user may be connected to the CPAP apparatus 200 and/or the mobile computing apparatus 205. Each of the sensor modules 310, 312 may be made up of several sensor modules. FIG. 6, for example, is a block diagram showing the sensor module 310 being connected to the CPAP apparatus 200 via the communication module 204 and configured to transmit sensor data to the CPAP apparatus 200. FIG. 7, for example, is a block diagram showing the sensor module 312 being connected to the mobile computing device 205 via the communication module 206 and configured to transmit sensor data to the mobile computing device 205. In some configurations, the CPAP apparatus 200 shown in FIG. 7 may not have a separate controller 203 for controlling an operation of the CPAP apparatus (as discussed above in paragraph [0078] with reference to the CPAP apparatus 300 shown in FIG. 5). In some configurations, the sensor modules 310, 312 and the modules 204, 205 can communicate through one or more types of wireless networks and associated protocols, including but not limited to WiFi, Bluetooth, and 2G/3G/4G. In some configurations, the sensor modules 310, 312 and the communication modules 204, 206 may communicate using a wired connection, such as a data transmission wire. In some configurations, the sensor modules 310, 312 and the communication modules 204, 206 may communicate via a USB, Ethernet, FireWire or serial port interface, for example but without limitation.

In some configurations, a visual sensor, such as the image sensor/camera 260, may be configured to transmit data corresponding to a patient's movements during a CPAP therapy session to a computing device accessible by, for example, a sleep therapist or other clinician. In some configurations, the visual sensor may be present on the mobile computing device 205 (like the image sensor/camera 260) and/or the CPAP apparatus 200, and the visual data may be transmitted to the clinician's computing device through the CPAP apparatus 200 and/or the mobile computing device 205 via a wireless or wired connection. In some configurations, the visual sensor may be separate from both the CPAP apparatus 200 and the mobile computing device 205, and the visual data may be transmitted to the clinician's computing device via the CPAP apparatus 200 (see FIG. 6) and/or the mobile computing device 205 (see FIG. 7). In some configurations, the visual data may be transmitted from the visual sensor to the clinician's computing device, without being transmitted through the CPAP apparatus 200 and/or the mobile computing device 205, via a wireless or wired connection. In some configurations the clinician's computing device may be a mobile computing device. In some configurations, the clinician's computing device may be remotely located from the patient and/or CPAP apparatus 200, such as in a sleep laboratory. The clinician may analyze and use the data to adjust the pressure and/or flow settings, for example, of the CPAP apparatus 200. In some configurations, the clinician's computing device may be configured to transmit data to the CPAP apparatus 200 through a wireless or wired data connection so the clinician can adjust the settings of the CPAP apparatus 200 without using the mobile computing device 205. In some configurations, the clinician's computing device may be configured to transmit data to the mobile computing device 205 through a wireless or wired data connection so the clinician can adjust the settings of the CPAP apparatus 200 through the mobile computing device 205.

In one embodiment, the CPAP apparatus 200 may be configured to sense and determine the magnitude and frequency of a power supply to the CPAP apparatus 200. This may be useful if the CPAP apparatus 200 is plugged into a power supply on an aircraft, for example. The CPAP 200 and/or the mobile computing device 205 may be configured to detect when reduced power may be available, and to reallocate the available energy to provide therapy with reduced or changed humidity, pressure control, and/or user interface functionality.

In one embodiment, the CPAP apparatus 200 may include means for supplying power to the mobile computing device 205. These means may include, but are not limited to, a power cable, a docking station capable of accepting the mobile computing device 205, and/or wireless electromagnetic induction-type charging unit, e.g. a Qi wireless charger.

Other ways in which the mobile computing device 205 may help to improve the patient's experience in using the CPAP apparatus 200 for therapy, as well as improve the patient's compliance to therapy, include but are not limited to those that are listed below:

In one embodiment, one or more of the CPAP apparatus 200, the mobile computing device 205, and associated sensor(s) are configured to transmit compliance data, therapy efficacy data, sensor data generated by the sensors and/or information corresponding to the sensor data to another computing device. The other computing device may be located remotely from the CPAP apparatus 200 and the mobile computing device 205, for example, and may be accessible by a clinician overseeing operation of the CPAP apparatus 200, for example, or another person. In some configurations, one or more of the CPAP apparatus 200, the mobile computing device 205 and the associated sensor(s) may be configured so the clinician or other person can interrogate one or more of the CPAP apparatus 200, the mobile computing device 205 and the associated sensor(s) using the other computing device to obtain the data. In some configurations, the CPAP apparatus 200, the mobile computing device 205 and/or the associated sensor(s) are configured to communicate with the other computing device through a wireless or wired data connection such as, for example but without limitation, through one or more communication or data links including WiFi, Bluetooth, 2G/3G/4G, the internet and a USB, Ethernet, FireWire or serial port interface. In some configurations, the clinician or other person can analyze the compliance data, therapy efficacy data, sensor data generated by the sensors and/or information corresponding to the sensor data, and adjust one or more operation parameters/therapy settings of the CPAP apparatus 200. In some configurations, the other computing device may be configured to communicate with the mobile computing device 205 so the clinician or other person can, using the other computing device, adjust the therapy settings of the CPAP apparatus 200 through the mobile computing device 205. In some configurations, the other computing device may be configured to communicate with the CPAP apparatus 200 (not through the mobile computing device) so the clinician or other user can adjust the therapy settings of the CPAP apparatus 200 without going through or using the mobile computing device 205.

In one embodiment, the mobile computing device 205 may be configured to interrogate the CPAP apparatus 200 for compliance data. In some configurations, the mobile computing device 205 may be configured to automatically interrogate the CPAP apparatus 200, such as at predetermined intervals or times. In some configurations, a patient or other user may operate the mobile computing device 205 to interrogate the CPAP apparatus 200. In some configurations, the compliance data from the CPAP apparatus 200 can then be provided/presented to the patient through the mobile computing device 205, such as via the user interface 207. In some configurations, the mobile computing apparatus 205 may be configured to use the compliance data, in combination with patient input, sensor data and/or remote data (such as from the internet) to automatically adjust one or more operation parameters/therapy settings of the CPAP apparatus 200. In some configurations, the mobile computing apparatus 205 may be configured to use the compliance data, in combination with patient input, sensor data and/or remote data, to suggest to/prompt a patient or other user to adjust one or more operation parameters/therapy settings of the CPAP apparatus 200.

In some configurations, the mobile computing device 205 may be used as a conduit memory on a remote cloud server. Memory on the mobile computing device 205, such as memory 241, may be used to store data such as, but not limited to, sensor data, patient settings, compliance data, and/or therapy efficacy data. In some configurations, the mobile computing device 205 may be configured to transmit the data through a wireless or wireless data connection to a remote cloud based service where it can be accessed in real-time, shared and analyzed. The mobile computing device 205 may be configured to automatically transmit, such as at predetermined intervals or times, the data to the remote cloud based service. In some configurations, the CPAP apparatus 200 or one or more sensor modules (e.g. sensor modules 310, 312) may be configured to transmit sensor data through a wireless or wireless data connection directly (not through the mobile computing device 205) to the remote cloud based service.

In one embodiment, the mobile computing device 205 may connect to the internet and/or use a GPS to locate the nearest CPAP apparatus service/consumable (wherein consumable refers to masks, tubing, and other respiratory device peripherals intended to have a relatively short lifetime) dealer, and communicate this information to the patient. This information may be given when requested by the patient, or may be relayed automatically when the mobile computing device recognizes a hardware fault or hardware obsolescence in the CPAP apparatus 200, or may be relayed automatically when the mobile computing device 205 recognizes that the intended lifespan of use of a consumable has been exceeded (for example, by checking records of past consumable orders, comparing the current time to the time at which the consumable was first used with the CPAP apparatus 200, and/or calculating the number of hours of therapy for which a particular consumable has been used). In some configurations, the mobile computing device 205 may connect to the website or order form that can display advertisements for new or old products when the need to service or replace is recognized. In some configurations, the mobile computing device 205 may be configured to directly connect the patient to a website or order form at which an order for service or consumables may be placed when the need to service or replace is recognized. In some configurations, the mobile computing device 205 may be configured to automatically place an order for service or consumable through connection to a website or order form for which such orders can be placed. In this manner, the patient may be able to find a more convenient place to service or buy consumables for the CPAP apparatus, particularly when traveling. In some configurations, the mobile computing device 205 may transmit a notification of the hardware fault/obsolescence to an equipment manufacturer or distributor, who may in turn communicate with the patient through the mobile computing device 205 with advertisements for new equipment, suggestions for use, and/or order forms.

In some configurations, the mobile computing device 205 may connect to the internet and/or use a GPS to access local climate and weather conditions, which could indicate the local temperature, humidity, and/or atmospheric pressure. If this data matches the temperature, humidity, and/or atmospheric pressure conditions of the local environment (e.g. room, or outside space) that the patient and/or the CPAP apparatus 200 is/are located in, the data may be used to facilitate control of the CPAP apparatus as mentioned above in paragraphs [0085], [0086], and [0087].

In some configurations, the mobile computing device 205 may provide help files, instructions, and/or education videos to the patient regarding the use of the CPAP device 200 and/or the mobile computing device 205. These instructions may be downloaded from the internet or may be accessed from a storage medium on the mobile computing device 205. In some configurations, the mobile computing device 205 may recognize from data sensed at the CPAP apparatus 200 or at the mobile computing device 205 that a therapy session was sub-optimal (e.g., a mask leak was excessive, patient compliance was poor, etc.) and may display help files, instructions, and/or related information regarding one or more reasons why the therapy session was sub-optimal.

In some configurations, the mobile computing device 205 may comprise an electronic game in which the patient may control a virtual avatar in a virtual world. In the electronic game, the patient may collect points or some other indicator of progress in the game, where the points or indicators may be obtained through compliant use of the CPAP apparatus 200. The points or indicators obtained may be used to advance the game or used as a virtual currency to purchase in-game benefits and/or prizes. Thus, the electronic game could provide an incentive to improve compliance of the patient.

In some configurations, the mobile computing device 205 may be configured to transmit (e.g. through use of the internet) data such as, but without limitation, patient and compliance data to a website that also hosts details of other patients and/or support groups. In some configurations, the website may be configured so patients can participate in challenges and/or compare compliance with other patients. For example, the website may have one or more patient leader boards based on points obtained by patients through compliant use of the CPAP apparatus 200 so patients can compare compliance and/or compete with other patients. In some configurations, the website may group patients, such as, but without limitation, patients of a similar demographic and state. In some configurations, the website may provide a range of metrics so patients can compare individual compliance against the average compliance of a group of patients. In some configurations, the website may be configured to filter and/or group patients intelligently based on, for example but without limitation, age, demographic and commodities, so patients feel their goals are attainable. In some configurations, the website may be configured to host challenges that patients can participate in through the mobile computing devices 205. For example, the website may host a compliance challenge for a group a patients that may go for set period (e.g. 30 days). In some configurations, the challenge may be open to patients who are of a similar demographic and/or condition, and/or located in the same region (e.g. town or city), and/or who are part of a common support group. For example, but without limitation, the challenge may require patients to reach a predetermined compliance threshold (e.g. 6 hours per night) every night for a month. In some configurations, the website is configured so patients can socially interact and track how they are going with the challenge compared to other patients, such as other patients in their region. In some configurations, the website is configured to so patients are challenged individually, without being compared to other patients. In some configurations, a patient can set individual challenges or goals to challenge themselves. In some configurations, the mobile computing device 205 may be configured so challenges and/or goals can be issued, such as by a remote cloud based service for example, to a patient through the user interface 207 of the mobile computing device 205. In some configurations, the website and/or remote cloud based service may be configured to host and/or issue challenges and/or goals that are specific to an individual patient and/or group of patients.

In some configurations, the mobile computing device 205 may obtain feedback from the patient through a questionnaire that may be answered after a CPAP therapy session. Questions on the questionnaire may include, for example, 'How did you sleep?' Did you have a dry mouth upon waking?' Was the air too hot?' Was the air too cold?' Was the air too dry?' and 'Was the air too wet?' The answers to such questions may be used to suggest CPAP apparatus operation parameter changes to the patient or may be used to automatically adjust the CPAP apparatus operation parameters.

In some configurations, the mobile computing device 205 may obtain feedback from the patient through a questionnaire that may be answered before a CPAP therapy session. Questions on the questionnaire may include, for example, 'How many alcoholic drinks did you have tonight, and when?' Are you stressed?' Have you had any caffeinated beverages today, and when?' What did you do before going to bed?' Did you exercise today?' What kind of exercise did you do today, and for how long did you do it?' 'What is your current body weight?' What is your height?' and 'What is your BMI?' Questionnaire results could be stored along with compliance data and therapy efficacy data, and/or could be tracked over time to suggest changes to CPAP operation parameters and/or could be displayed to the patient to give the patient an understanding of how his/her lifestyle choices affect the quality/duration of sleep and/or compliance to therapy. Likewise, this information could be sent in real-time over the internet, or in packets through use of the internet or a storage medium, to a health professional, medical device distributor, medical device manufacturer, or other person who may analyze the data and use the analysis to make lifestyle suggestions to the patient or otherwise find ways to improve the therapy experience for the patient.

In some configurations, the mobile computing device 205 may comprise hard drive space that may be used to receive and store information obtained, for example but without limitation, from the CPAP apparatus 200, from the patient, from the internet, or via a 2G/3G/4G network. This information may regularly (e.g. after predetermined amounts of time) or in real-time be sent to a health professional, medical device distributor, medical device manufacturer, polysomnography laboratory technician, or other person for analysis. A data connection may be established in which information can be transferred from the CPAP apparatus 200 to the mobile computing device 205 associated with the CPAP apparatus, and then from the mobile computing device 205 associated with the CPAP apparatus to the internet or another mobile computing device, or vice versa, e.g. from the internet or another mobile computing device to the mobile computing device associated with the CPAP apparatus 200, and then from the mobile computing device 205 associated with the CPAP apparatus 200 to the CPAP apparatus 200. Thus, the mobile computing device 205 associated with the CPAP apparatus 200 (e.g., the patient's mobile computing apparatus 205) may be used to assist in polysomnography lab titrations, providing medical advice, or otherwise find ways to improve the therapy experience for the patient.

In some configurations, a memory storage device that is separate to the mobile computing device 205 may be used to receive and store information from the CPAP apparatus 200, from the mobile computing device 205, from the patient, and/or from the internet. The memory storage device may be integrated into the housing of the CPAP apparatus 200. Alternatively, the memory storage device may be a separate to the CPAP apparatus 200. The CPAP apparatus 200 and/or the mobile computing device 205 may be configured for communication with the memory storage device through a wireless or wired data connection. In one example form of the memory storage device, the memory storage device may be a USB drive or an SD card. The memory storage device may comprise an indicator that emits a signal, such as a visual or audible signal, when the memory storage device is connected to the CPAP apparatus 200 and/or the mobile computing device 205. For example, the indicator may comprise a light to indicate when the mobile storage device is initially connected to the CPAP apparatus 200 and/or the mobile computing device 205. The indicator may be configured so that the light fades away over time.

In some configurations, the mobile computing device may receive output from the CPAP apparatus 200 where the CPAP apparatus 200 has detected an adverse condition (e.g. an empty humidification chamber 105 (if present), leaking at the mask 107 or around tubing 106) and make the patient aware of such a condition through the use of an audial, a tactile and/or visual indicator (wherein the audial indicator could, for example, be a sound at a preset volume played on the mobile computing device 205, a voice message, or some other indicator, the tactile indicator could be one or more vibrations, and the visual indicator could be a graphical user interface message, icon, a bright and/or flashing color, or some other indicator). The audial, tactile and/or visual indicator may occur immediately or after having detected the adverse condition for a period of time.

In some configurations, the mobile computing device 205 may access the patient's calendar on the mobile computing device 205 and look for upcoming national holidays and memos/notes regarding vacation plans, business trips, and other occasions during which the patient might be expected to be away from home. When the current date is close to or matches one of these times, the mobile computing device 205 may output an audial, tactile and/or visual message. In some configurations, the message may remind the patient to take the CPAP apparatus if traveling and/or to empty the humidification chamber 105 (if present) before traveling with the CPAP apparatus 200.

In some configurations, the mobile computing device 205 may transmit data sensed by the CPAP apparatus 200 or by the mobile computing device 205 to household electronic devices and/or appliances that are capable of communication with the mobile computing device 205 through a wireless or wired data connection. In some configurations, the mobile computing device 205 and/or the CPAP apparatus 200 can automatically adjust and/or turn off and/or on the household electronic devices and/or appliances based on the data sensed by the CPAP device 200 or mobile computing device 205. In some configurations, the household electronic devices and/or appliances may adjust and/or turn off and/or on based upon the transmitted data. Such household electronic devices and/or appliances may comprise, for example, coffee machines, light fixtures, televisions, media players, vacuum cleaners, computers, radios, heaters, air conditioners, and/or heat pumps. In some configurations, the CPAP apparatus 200 could sense the wakefulness of the patient through conditions sensed at the CPAP apparatus 200 (e.g., using any suitable algorithm capable of or adapted to sense a sleep state of a patient) and communicate this sensory data to the mobile computing device 205, which in turn may send a signal to the household electronic device and/or appliance adjusting and/or turning off and/or turning on the household electronic device or appliance. The mobile computing device 205 and/or the CPAP apparatus 200 may be configured to automatically decrease the brightness of a backlight of a display of the CPAP apparatus 200, if the CPAP 200 has a display with a backlight, if the mobile computing device 205 and/or CPAP apparatus 200 senses that the patient has fallen into a slumber. Alternatively, the mobile computing device 205 and/or the CPAP apparatus 200 may be configured to increase the brightness of the display when the mobile computing device 205 and/or the CPAP apparatus 200 senses the patient is waking. A backlight of a display of the CPAP apparatus 200, for example, if the display has a backlight, may be turned on and off. The brightness of the graphical user interface 208 may be similarly turned off and on when the patient is waking and falling into a slumber. A television could be muted or turned off as the CPAP apparatus 200 senses that the patient has fallen into slumber for example, or likewise a light fixture may be dimmed or turned off under similar conditions. In this manner, the patient's sleep hygiene and therapy experience may improve through use of communication between the CPAP apparatus 200, the mobile computing device 205, and/or the household electronic device and/or appliance. In some configurations, the mobile computing device 205 may transmit data to and/or receive data from another mobile computing device or device (including, but not limited to, 'intelligent' blood pressure measurement devices and 'intelligent' weight scales) to facilitate the sharing of any data that would be useful for the devices involved.

In some configurations, the mobile computing device 205 may accept input regarding the particular interface (e.g., mask) being used with the CPAP apparatus 200. The mobile computing device 205 may then look up characteristics of the interface (e.g., mask), including predicted leak rates, either from a database containing one or more sets of data corresponding to the interface (e.g., mask) that has been loaded onto the mobile computing device 205 or from a similar database found on the internet, for example but without limitation. The mobile computing device 205 may use, for example, the predicted leak rate for a particular interface (e.g., mask) to suggest changes to the pressure and/or flow of the gas propelled by the CPAP apparatus 200 through the interface. In some configurations, the mobile computing device 205 may communicate with the CPAP apparatus 200 to automatically make compensatory changes to the pressure and/or flow of the gas. Thus, if the patient is switching between interfaces for which data can be found (e.g., on the database), the patient may be more readily change between interfaces and receive adequate pressure and/or flow while compensating for characteristics of the interfaces that might create variations in pressure and/or flow delivered to the patient.

In some configurations, the mobile computing device 205 may accept sensor data from the CPAP apparatus 200 or may observe characteristics (e.g., sounds) indicating a mask or breathing conduit leak. In this situation, the mobile computing device 205 may instruct the CPAP apparatus 200 to increase the pressure to compensate for the leak. In this manner, the patient may receive adequate pressure while compensating for leaks within the breathing circuit (i.e., the breathing conduit and/or the mask).

In some configurations, the mobile computing device 205 may accept sensor data from the CPAP apparatus 200 or may observe characteristics (e.g., sounds) indicating a mouth leak. In this situation, the mobile computing device 205 may instruct the CPAP apparatus 200 to adjust the pressure to compensate for the leak. In this manner, the patient may be relieved of unnecessarily applied pressure.

In some configurations, the mobile computing device 205 may (e.g., through use of the internet) direct the patient to support groups found on social media websites, for example but without limitation. The support group chosen may be selected according to answers to one or more questions presented to the patient through the mobile computing device 205. Alternatively or in addition to the above, the support group chosen may be influenced by the operation parameters of the CPAP apparatus 200 and/or patient data stored on the mobile computing device 205 (which may comprise at least one or more of the following: age, height, weight, BMI, and/or compliance).

In some configurations, the mobile computing device 205 may sync the time, date, location and/or calendar of the CPAP apparatus 200 and the mobile computing device 205 if both the apparatus 200 and the device 205 comprise a time, date, location and/or calendar. The CPAP apparatus 200 and/or the mobile computing device 205 may be configured to connect to the internet and/or use a GPS to obtain the time, date, location and/or calendar. In some configurations, the CPAP apparatus 200 and/or the mobile computing device 205 may estimate one or more ambient conditions, such as temperature, for example, based on the time, date, location and/or calendar. The CPAP apparatus 200 and/or the mobile computing device 205 may adjust operational parameters of the CPAP apparatus 200 based on the estimated ambient conditions. In winter for example, when it is generally colder and more humid than in summer, the humidity settings of the CPAP apparatus 200 may be adjusted to prevent rain-outs. In some configurations, the CPAP apparatus 200 and/or the mobile computing device 205 may be configured to adjust the brightness of a display of the CPAP apparatus 200, if the CPAP apparatus 200 has a display, using the time, date, location and/or calendar. The CPAP apparatus 200 and/or the mobile computing device 205 may be configured to automatically increase the relative brightness of the display in winter and/or at night for example, and decrease the relative brightness of the display in summer and/or daylight hours. The environment around the CPAP apparatus 200 is likely to be relatively darker at 5 pm in winter than at 5 pm in summer, for example, so it may be desirable for the display to have a brighter default setting in winter. The surrounding environment is similarly likely to be relatively lighter at noon than in the evening, for example.

In some configurations, the mobile computing device 205, when connected to the CPAP apparatus 200, may be configured to be automatically set to a 'silent' or 'sleep' mode, which may silence any sounds that may interrupt the patient's therapy session. In this manner, the patient may sleep without undue interruption.

In some configurations, the mobile computing device 205 may connect to the internet, for example but without limitation, and download a software update and/or modification for the mobile computing device 205 and/or the CPAP apparatus 200. The mobile computing device 205 may notify the patient if such an update and/or modification can be made and request permission to install the update and/or modification. In some configurations, the mobile computing device 205 may automatically update and/or modify the software for the mobile computing device 205 and/or the CPAP apparatus 200. In some configurations, the mobile computing device 205 may upload a software upgrade and/or modification for the mobile computing device 205 and/or the CPAP apparatus 200 from a storage medium (e.g. floppy discs, USB drives, zip drives, SD cards, etc).

In some configurations, the CPAP apparatus 200 may be configured to transmit sensor data to the mobile computing device 205, such as data from one or more sensors integrated into, associated with and/or connected to the respiratory device and configured to generate data representing an operating condition of the humidifier 201, the blower 202, the breathing conduit 106 leading to the patient interface 107, and/or an end-of-hose sensor module/cuff, if present, connecting the conduit 106 to the interface 107. In some configurations, the mobile computing device 205 may be configured to process at least one sleep algorithm for the control of the CPAP apparatus 200, rather than the controller 203 processing the sleep algorithm. In some configurations, the mobile computing device 205 may be configured to enable cloud-based processing of the sleep algorithm.

In some configurations, the mobile computing device may, if playing music or other audio files for the patient from a music database while the patient is undergoing therapy, use sensor data (e.g. pressure and/or flow data, etc) obtained at the CPAP apparatus 200 and/or sensor data obtained at the mobile computing device 205 (e.g. image and/or sound data) to determine the wakefulness state of the patient, and reduce the volume to a lower level or zero as the patient falls into slumber. Alternatively or in addition to the above, the mobile computing device 205 may reduce the volume of the music to a lower level or zero over a predetermined amount of time from the start of a therapy session. Alternatively or in addition to the above, the mobile computing device 205 may contain two or more music databases containing different varieties of music, and choose a song to play based on the predetermined amount of time, the wakefulness state of the patient, or the respiration rate of the patient, which may be determined from the flow and/or pressure data sensed at the CPAP apparatus 200. For example, if the mobile computing device 205 contains two music databases, the first containing rock music and the second containing lullabies, the mobile computing device 205 may choose to transition from the first set to the second set as the patient falls into slumber, or over a predetermined amount of time from the start of a therapy session, or as the respiration rate of the patient slows (which may result as a physiological consequence of the patient falling into slumber). In this manner, the patient may be able to transition into sleep more easily while enjoying listening to music on or from the mobile computing device 205.

In some configurations, the patient may use the mobile computing device 205 to set an alarm for a predetermined time, which may be used to wake the patient from a sleep session. However, waking the patient when the patient is in a relatively deep sleep state may make the patient feel groggier and/or more tired as opposed to waking the patient when the patient is in a relatively shallow sleep state, even if the total sleeping time is greater in the first instance. In some configurations, the patient may use the mobile computing device 205 to set an audio, tactile and/or visual alarm for a predetermined range of times (e.g. 5:30 am to 7:00 am, etc) and prompt the mobile computing device 205 to wake the patient based on sensor data obtained from the CPAP apparatus 200 and/or the mobile computing device 205 indicating the sleep stage of the patient. The patient may define the shallow and deep sleep states manually through the mobile computing device 205 or use a predetermined configuration defining the distinction between a 'shallow' and/or a 'deep' sleep state. Such a predetermined configuration may be set up by a physician, an equipment distributor, and/or a manufacturer. In this manner, the patient may be roused at a time within the selected time range but before the end of the range if the CPAP apparatus 200 and/or the mobile computing device 205 detects the patient in a relatively shallow sleep state and communicates this information to the mobile computing device 205. If the patient remains in a relatively deep sleep state over the predetermined range of times, then the alarm may simply rouse the patient at the end of the predetermined range of times. In this manner a patient may take advantage of the CPAP apparatus 200 to wake from sleep feeling more rested while resolving to rise at or earlier than a predetermined time.

In some configurations, the patient may use the mobile computing device 205 to set an alarm for a first predetermined time, which may be used to wake the patient from a sleep session. The CPAP apparatus 200 may in turn start to decrease or ramp down the pressure and/or flow of the gases propelled through the apparatus at a second predetermined time (e.g. a predetermined number of minutes, etc) before the first predetermined time, and arrive at a minimum pressure and/or flow at the time of the alarm.

In some configurations, the CPAP apparatus 200 and/or the mobile computing device 205 may be configured to communicate with a patient indicator device 270 through a wireless or wired data connection. Preferably the CPAP apparatus 200 and/or the mobile computing device 205 are configured to communicate with the patient indicator device 270 through a wireless data connection. The patient indicator device 270 may be a wearable device, such as a wearable wristband. The patient indicator device 270 may have a vibrator, or other tactile, audible or visual indicator. In some configurations, the CPAP apparatus 200 may sense the wakefulness of the patient through conditions sensed at the CPAP apparatus 200 and communicate this sensory data to the mobile computing device 205. When the CPAP apparatus 200 and/or the mobile computing device 205 determines that the patient is waking after a night of sleep/session of therapy or an alarm is about to go off for example, the CPAP apparatus 200 and/or the mobile computing device 205 can transmit a signal to the indicator device that triggers the indicator device 270 to vibrate for example, to noiselessly wake the patient.

In some configurations, the mobile computing device 205 may, if desired by the patient, stop wireless communication between the CPAP apparatus 200 and the mobile computing device 205 while the CPAP apparatus 200 detects that the patient is sleeping. Such configurations may help to allay fears of patients who may believe that radiation generated from the mobile computing device 205 and/or the CPAP apparatus 200 while the patient is asleep may cause discomfort and/or bodily harm (e.g. cancer, etc).

In some configurations, the mobile computing device 205 or another computing device may be configured to wirelessly obtain information about components of or for use with the CPAP apparatus 200, such as the interface (e.g. mask) 107, the conduit 106 and/or a humidifier 201. In some configurations, the mobile computing device 205 or other computing device may comprise a radio-frequency identification (RFID) reader, and the components may each comprise an interrogatable RFID chip (or 'tag') integrated into or located on the component. The tag may have local memory that stores product information about the component, including but not limited to, the product family, model number and serial number. In some configurations, the mobile computing device 205 or other computing device may be a near field communication- (NFC-) enabled device and the chips may be NFC tags embedded in the components. The mobile computing device 205 or other computing device may retrieve the product information stored on the NFC tag. The mobile computing device 205 or other computer may the transfer the product information to the CPAP apparatus 200 through a wireless or wired data connection. If the CPAP apparatus 200 is an NFC-enabled device, the mobile computing device 205 or other computer may transfer product information through an NFC connection. Alternatively, the mobile computing device 205 or other computer may transfer the product information through a wired or another wireless data connection, such as a WiFi or Bluetooth connection. If the CPAP apparatus 200 is an NFC-enabled device, an NFC connection may be used to automatically establish and authenticate the WiFi or Bluetooth connection without the need for a user to enter a password. In some configurations, the mobile computing device 205, other computing device and/or CPAP apparatus 200 may look up further product information about the component from a database, such as a database found on the internet. The CPAP apparatus 200 and/or the mobile computing device 205 can use information retrieved from the NFC tag about the component, such as leak characteristics for a patient interface 107 for example, when processing a sleep algorithm.

In some configurations, wirelessly interrogatable memory, such as RFID and/or NFC tags embedded in components of or for use with the CPAP apparatus 200, may be used for verification of authenticity via a unique ID code stored on each tag, such as through the internet. In some configurations, the unique ID code may be a serial number. Advantageously, this may provide traceability and prevent counterfeit products. The unique ID code may also be used for expiration date verification and preventing re-use. The unique ID code may also be useful when ordering replacements parts, because the unique ID code can be used to identify the existing part. Using the mobile computing device 205 or another computing device, clinician staff or wholesalers can also record the unique ID code when shipping by automatically uploading that information. The uploaded information could be used for product warranties, for example.

In some configurations, the CPAP apparatus 200 is configured to be wirelessly configured with a patient's settings and/or data relating to one or more components of or for use with the CPAP apparatus 200 when the CPAP apparatus 200 is tuned off (unpowered). The CPAP apparatus 200 may comprise an embedded smart NFC tag having local memory, for example. The mobile computing device 205, if NFC-enabled, or another NFC-enabled computing device may configure the CPAP apparatus 200 by uploading/updating the local memory of the NFC tag with a patient's settings and/or data relating to one or more components using an NFC connection. Advantageously, the CPAP apparatus 200 may be configured using an NFC connection while the CPAP apparatus 200 is turned off and inside packaging. The smart NFC tag may get its power from the interrogating RF signal. In some configurations, the smart NFC tag has a microprocessor interface so that when the CPAP apparatus 200 is turned on (powered up), the controller 203 can interrogate the local memory of the NFC tag and update the settings of the CPAP apparatus 200 for the patient and/or component(s). These settings could include pressure settings, and information about the interface 107, conduit 106 and/or other components if previously obtained, for example.

In some configurations, the CPAP apparatus 200 may be configured to store diagnostic information or other information in the local memory of the NFC tag. Advantageously, this may facilitate fault finding because the local memory can be interrogated by an NFC-enabled device without powering up the CPAP apparatus 200. Due to a fault in the CPAP apparatus 200 for example, it may not be possible to power up the apparatus 200. Advantageously, this flight recorder-like function may also save time in recording and verifying fault codes and the conditions leading up to the fault. End users could upload this information, such as with the mobile computing device 205 or another computing device through an NFC connection, providing opportunities for data mining usage patterns, performance information, fault information, and/or reliability information.

Certain features, aspects and advantages of an embodiment of the present invention have been described with reference to a respiratory device in the form of a CPAP apparatus 200, particularly for use in the treatment of obstructive sleep apnea. However, certain features, aspects and advantages of a mobile computing device 205 as described above may be advantageously used with other therapeutic or non-therapeutic breathing devices, such as ventilators, or for the treatment of other conditions, such as COPD. Certain features, aspects and advantages of the method and apparatus of the present disclosure may be equally applied to other breathing devices for other conditions.

Similarly, certain features, aspects and advantages of the disclosure have been described with reference to a mobile computing device 205. However, certain features, aspects and advantages of the methods and apparatus of the present disclosure may be applied to a non-mobile computing device (e.g. a desktop computer, a stationary terminal, etc.) provided that the non-mobile computing device can be positioned relative to the patient and the CPAP apparatus in such a manner that it is capable of performing the aforementioned functions of the mobile computing device.

Certain features, aspects and advantages of the present disclosure have been described with reference to a patient receiving information from the mobile computing device regarding operation parameters of a CPAP apparatus or controlling operation parameters of a CPAP apparatus from the mobile computing device. However, certain features, aspects and advantages of such methods may be advantageously practiced by a physician, medical staff member, equipment distributor, or other person on behalf of the patient. For example, a physician using a separate computing device capable of communicating with the mobile computing device or the CPAP apparatus may receive information instead of or along with the patient and may use the information to assist in suggesting treatment regimens for the patient, or the physician may use the separate computing device to adjust CPAP apparatus operation parameters, either through the mobile computing apparatus or directly with the CPAP apparatus. Thus many of the methods and apparatus described herein may be altered to be applied by persons aside from the patient.

If travelling, the patient will typically take the CPAP apparatus with them. The various components of the CPAP may be carried in a bag. Usually, the patient will empty the humidification chamber 105 (if present) before travelling with the CPAP apparatus 200. However, some water may remain in the chamber, or the patient may forget to empty the chamber 105. The water may leak or spill out of the reservoir during travel and into the bag. There is a surface break/fissure along the frame of the CPAP unit through which water can potentially enter the unit and disrupt the internal printed circuit board. If the CPAP unit is carrying water and the unit is transported in an ordinary container, the unit could spill water that will sit in the container and may seep into the unit through the break or elsewhere.

Figure 8:
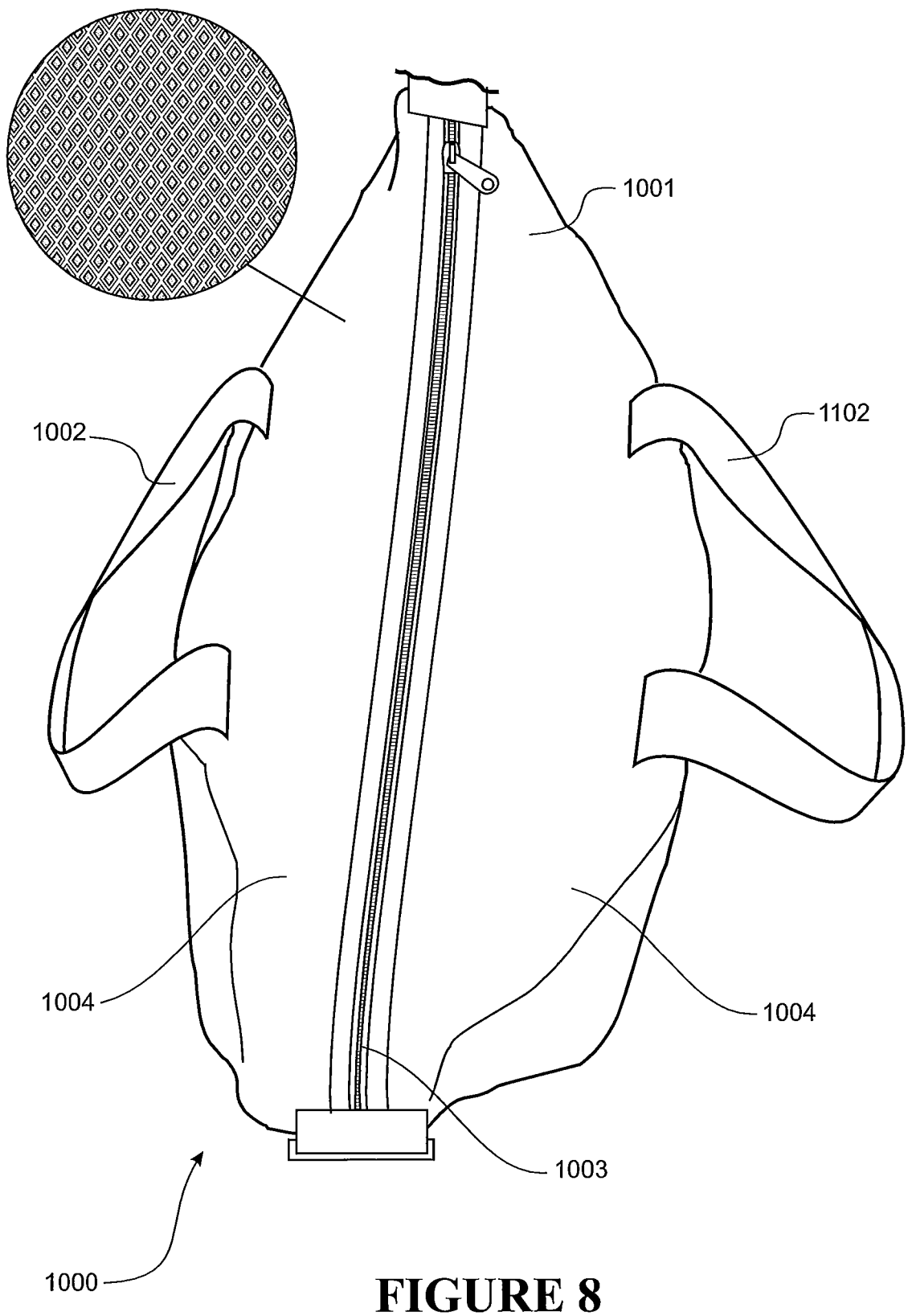
FIG. 8 is a perspective view of a first preferred embodiment bag for managing water that leaks or spills out of a humidification chamber of a CPAP unit.

FIG. 8 shows a first preferred embodiment bag 1000 for managing water that leaks or spills out of the humidification chamber 105. The first preferred embodiment bag 1000 does not substantially retain water. The body 1001 of the bag 1000 is formed from three layers of material, which are described in more detail below. The bag has a pair of carry handles 1002, formed from strapping or webbing material. Alternatively, the handles 1002 may be formed from a similar material to the body 1001 of the bag. The bag 1000 has a substantially flat and rectangular base, four side walls extending upwardly from the base, and an opening. The opening of the bag is closed by a zipper 1003.

Figure 9:
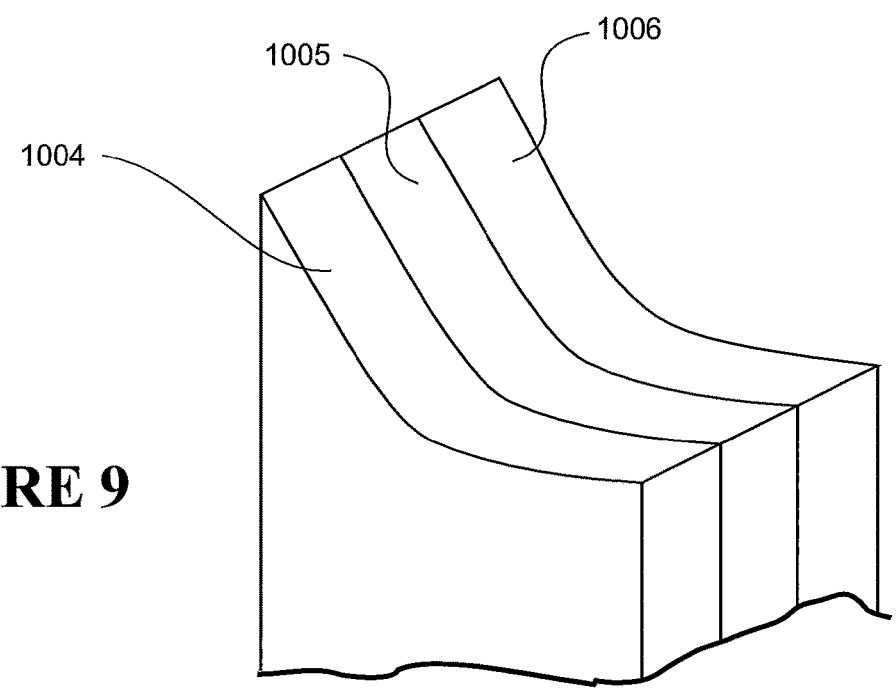
FIG. 9 is a schematic view of layers of material forming the bag of FIG. 8.
Figure 10:
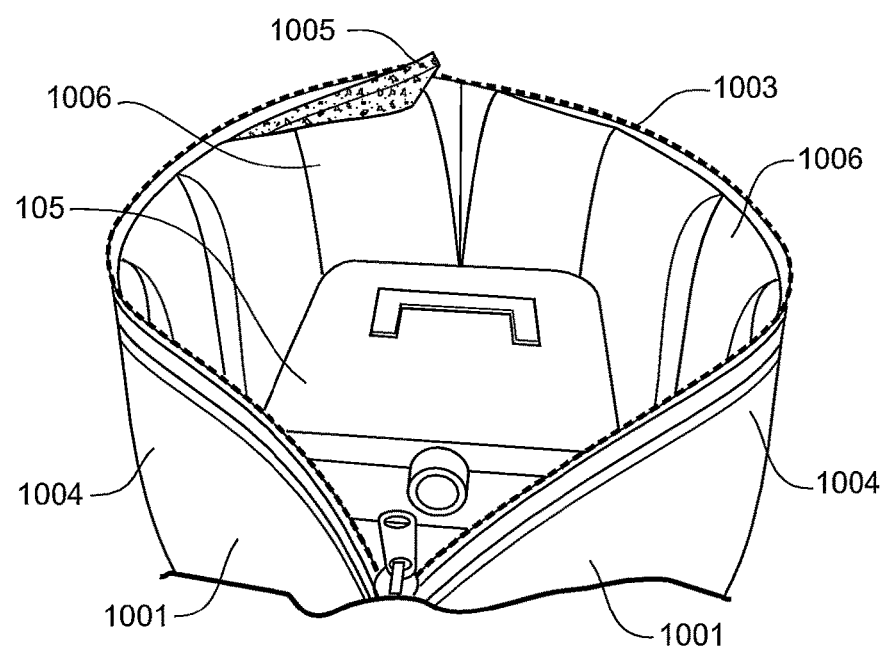
FIG. 10 is a partial perspective view of the bag of FIG. 8 showing the foam later pulled out from between the two adjacent layers.
Figure 11:
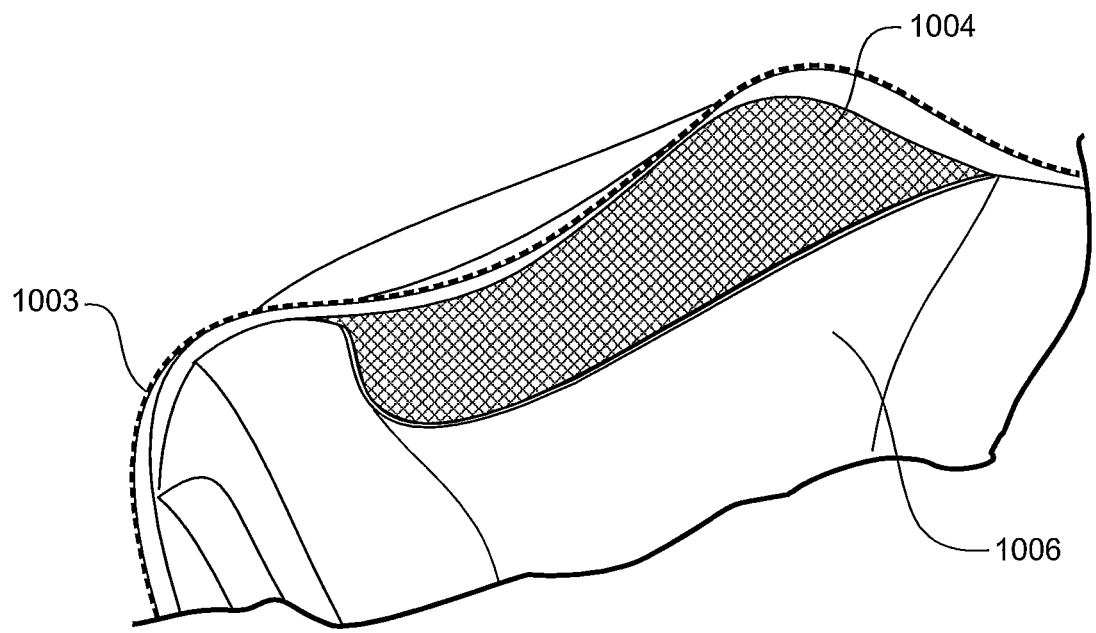
FIG. 11 is a detail view of the bag of FIG. 8 with the foam removed.
Figure 12:
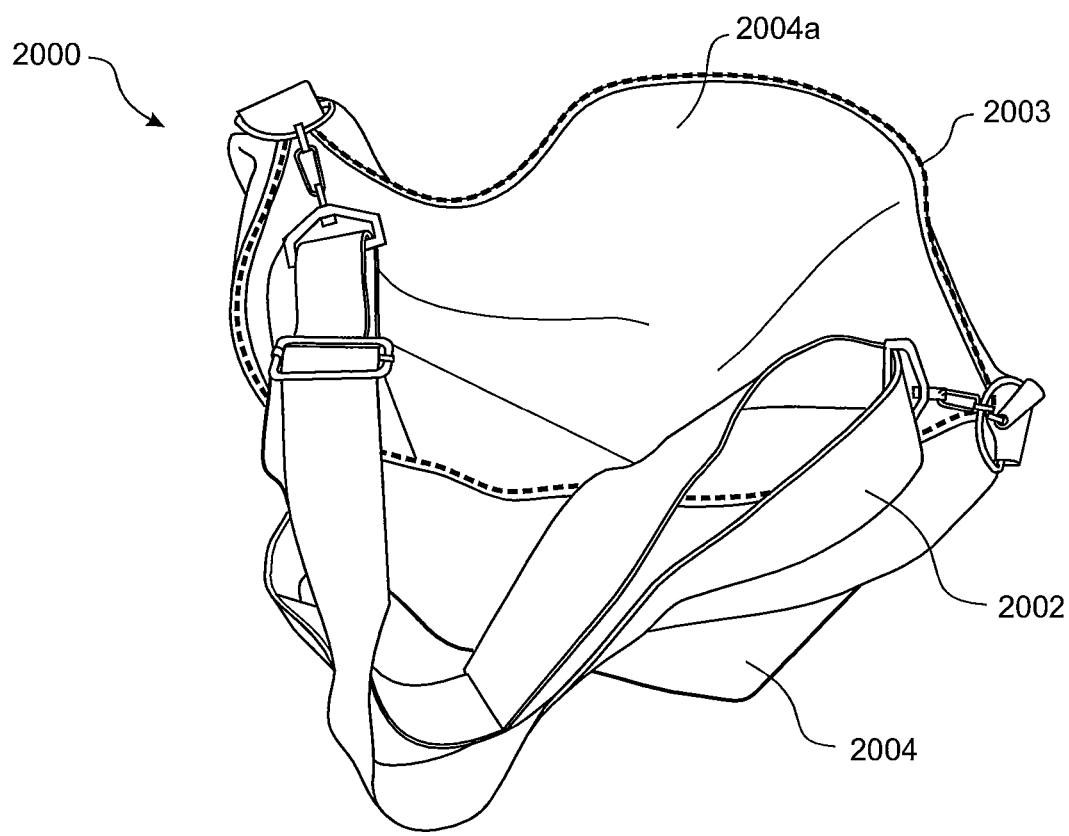
FIG. 12 is a perspective view of a second preferred embodiment bag for managing water that leaks or spills out of a humidification chamber of a CPAP unit.
Figure 13:
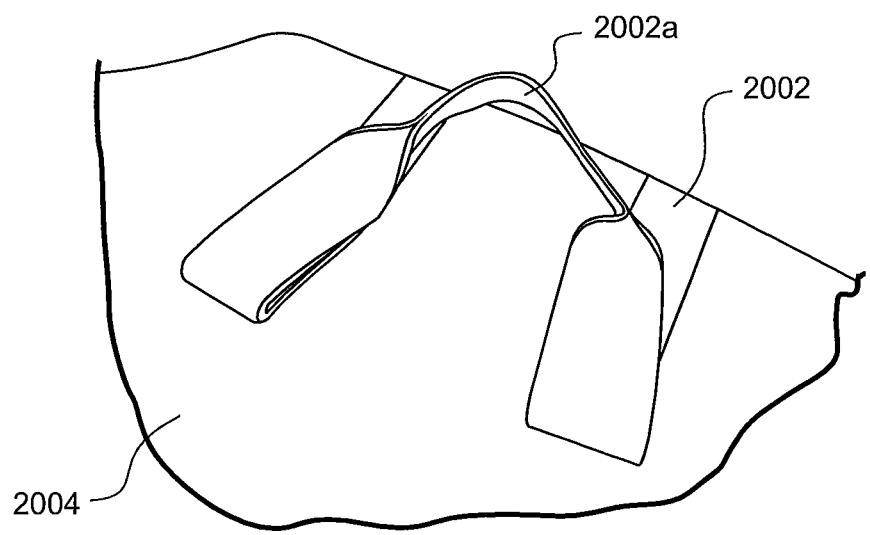
FIG. 13 is a detail view of the carry handle of the second preferred embodiment bag of FIG. 12.
Figure 14:
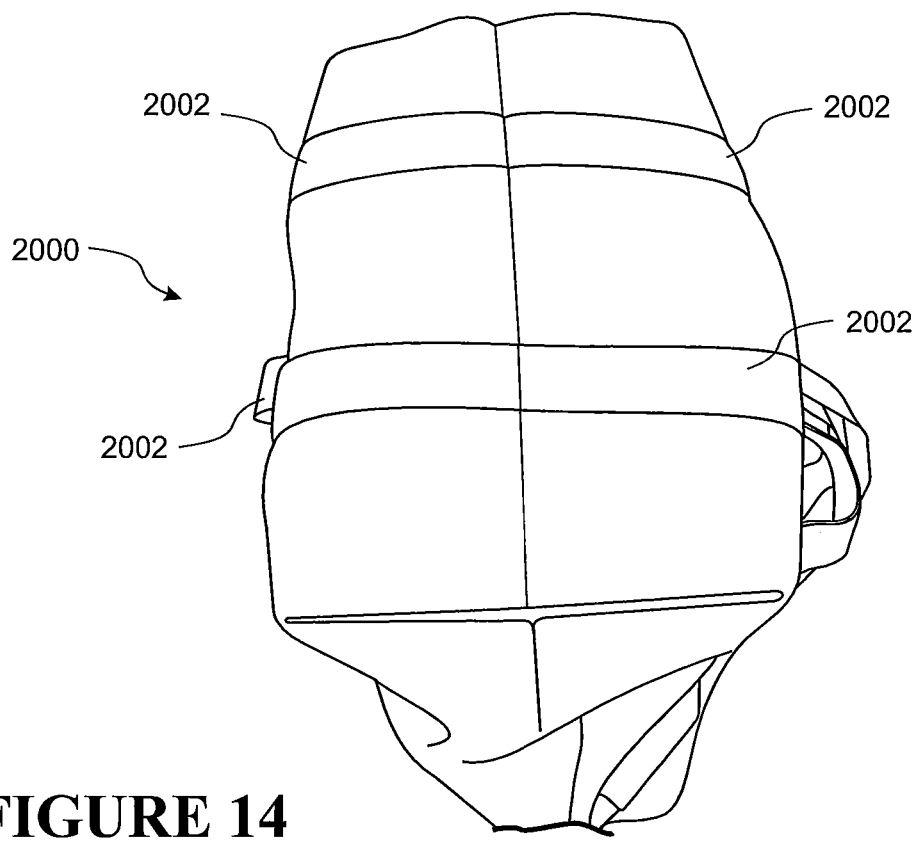
FIG. 14 is a bottom perspective view of the bag of FIG. 12.
Figure 15:
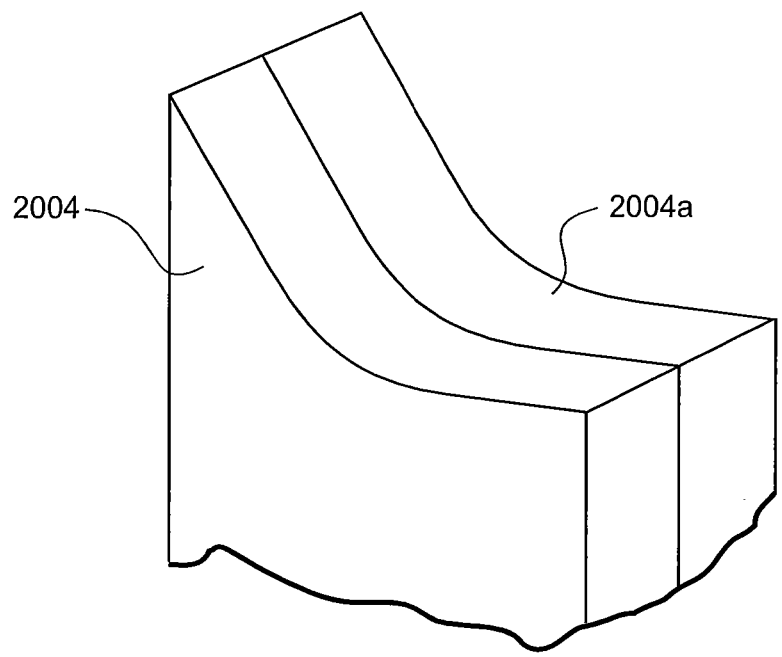
FIG. 15 is a schematic view of layers of material forming the bag of FIG. 12.

With reference to FIG. 9, the bag is constructed from three layers of material in the following order: an outer layer of mesh 1004, a middle layer of open cell foam 1005, and an inner layer of fabric 1006. All of the materials have some degree of porosity:

It will be appreciated that the first preferred embodiment bag allows water spilled in the bag to dry quickly. Water has been poured into a prototype, most of which fell through the bag. The retained moisture quickly dried due to the breathable design of the bag.

As shown in the detail view of FIG. 8, the outer appearance of the bag is an external porous mesh material. The outer layer of the bag is a mesh fabric, which is known as 'Sandwich mesh', 'air mesh', or 'knitted spacer textile'. The mesh has two layers two layers of multifilament mesh knits connected with lengths of spacer fibers. The mesh may be constructed from polyester fibres, which may also include other fibre compositions such as nylon or spandex. One example of a suitable, commercially available spacer mesh product is '3mesh' produced Müller Textil GmbH. The outer layer of the bag shown in FIGS. 8 to 11 is the mesh fabric described above. Although the mesh fabric is not specifically shown in FIGS. 8 to 11, except in the detail view, it will be understood that the outer layer comprises the mesh material.

In the preferred embodiment, the inner layer 1006 is a polyester 65% cotton 35% fabric blend, which is breathable while still providing some structural support. Alternatively, the inner layer 1006 may have more polyester or more cotton. Other suitable fibres may be used for the inner layer 1006, for example, rayon fibres may be used in addition to cotton fibres or as an alternative to rayon fibres. The inner layer may be formed using known manufacturing techniques, such as weaving or knitting.

The open cell foam 1005 is a foam in which the cells or gas pockets within the foam are connected to each other, allowing water to flow through the foam. The foam 1005 is suitably polyurethane foam. The foam 1005 may be placed in an opening formed between the mesh 1004 and inner fabric layer 1006 and sit in that opening. Alternatively, the foam 1005 may be attached to one or both of the other layers, for example, by stitching or gluing.

Any one or all of the layers 1004, 1105, 1006 may be a flame-retardant material, an anti-static material, or an anti-bacteria material, for example.

In alternative embodiments, the bag 1000 may be formed from a single layer or double layers of breathable material. In these embodiments, additional structural support for the bag may be provided. The additional structural support may take the form of a frame around which the material is supported, or may take the form of ribs or stays attached to the material.

An example of a double layer bag is the second embodiment of the bag 2000 shown in FIGS. 12 to 15. Unless described as otherwise below, the features and functioning of the bag should be considered the same as described for the first embodiment above, and like reference numerals indicate like parts with the addition of 1000.

The second embodiment of the bag 2000 has handles 2002 in which the intermediate portion 2002a is doubled over itself to form a grip portion. The side handles 2002 run along the bottom of the bag and connect at the bottom of the bag, that is, both handles are integrally formed as one piece. The handles 2002 are stitched to the bottom along the centre of the bag. It will be appreciated that the multiple separate straps may be used in an alternative embodiment. The bottom stitching provides some structural support to the bag.

The handles 2002 may be formed from the same material as the body of the bag, or may be formed from strapping or webbing material. The strapping may be reinforced with stitching.

In a third preferred embodiment, the bag 3000 may be adapted to absorb water spilled in the bag rather than encouraging water to travel though the bag material, as described above in relation to the first two preferred embodiments. Unless described as otherwise below, the features and functioning of the bag should be considered the same as described for the first embodiment above, and like reference numerals indicate like parts with the addition of 2000.

The third preferred embodiment bag 3000 may contain accidental spills from the humidifier of the CPAP unit. This embodiment confines spilled water to localized regions of the bag 3000. That will prevent, or at least substantially inhibit, spilled water from entering the CPAP unit frame and disrupting the internal electronics of the CPAP unit.

Figure 16:
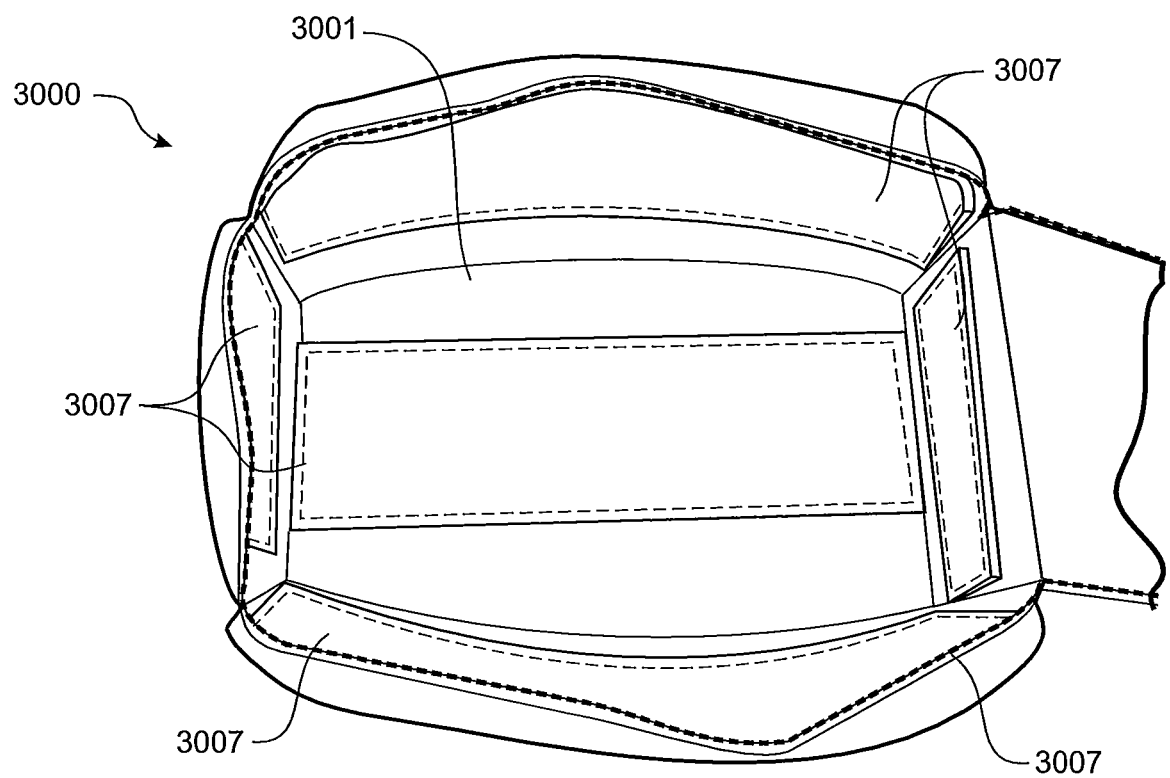
FIG. 16 is a partial perspective view of a third preferred embodiment bag for managing water that leaks or spills out of a humidification chamber of a CPAP unit.

The bag 3000 is formed from any suitable material and sponges 3007 are attached to the body of the bag. FIG. 16 shows the sponge 3007 stitched directly to the body of the bag. Alternatively, the sponges 3007 may be held in pockets of the bag. For example, parts of the interior of the bag 3000 may have a mesh cover that contains the sponge 3007. The water will be drawn through the mesh and then absorbed by the sponge 3007.

In the preferred embodiment shown, the sponge is attached to the body of the bag 3000. Alternatively, the absorbent material may be removable from the bag 3000. When the absorbent material is removable, it may be either re-usable or disposable.

With reference to FIG. 16, a front view of the open bag 3000 is shown in which the sponge material 3007 is positioned within the sides and bottom of the interior surface of the bag. It may be possible to have the entire interior surface of the bag 3000 covered with the sponge 3007 including the lid, rather than just parts thereof. In another alternative, the sponge 3007 may be positioned in only the base of the bag. In a further alternative, the entire body of the bag 3000 may be formed from sponge or other hydrophilic material.

The third embodiment has been described as having a hydrophilic material in the form of a sponge material. Any absorbent material could be used within the bag. For example, the sponge may be polyurethane foam, a natural sponge, or an absorbent pad.

The third embodiment allows water spilled in the bag to be retained in the bag 3000 rather than enter the CPAP unit. In an informal demonstration, water was poured into a prototype bag 3000, most of which was retained in the sponge material in the bag.

The body of the bag may be formed from one or more layers of fabric.

Figure 17:
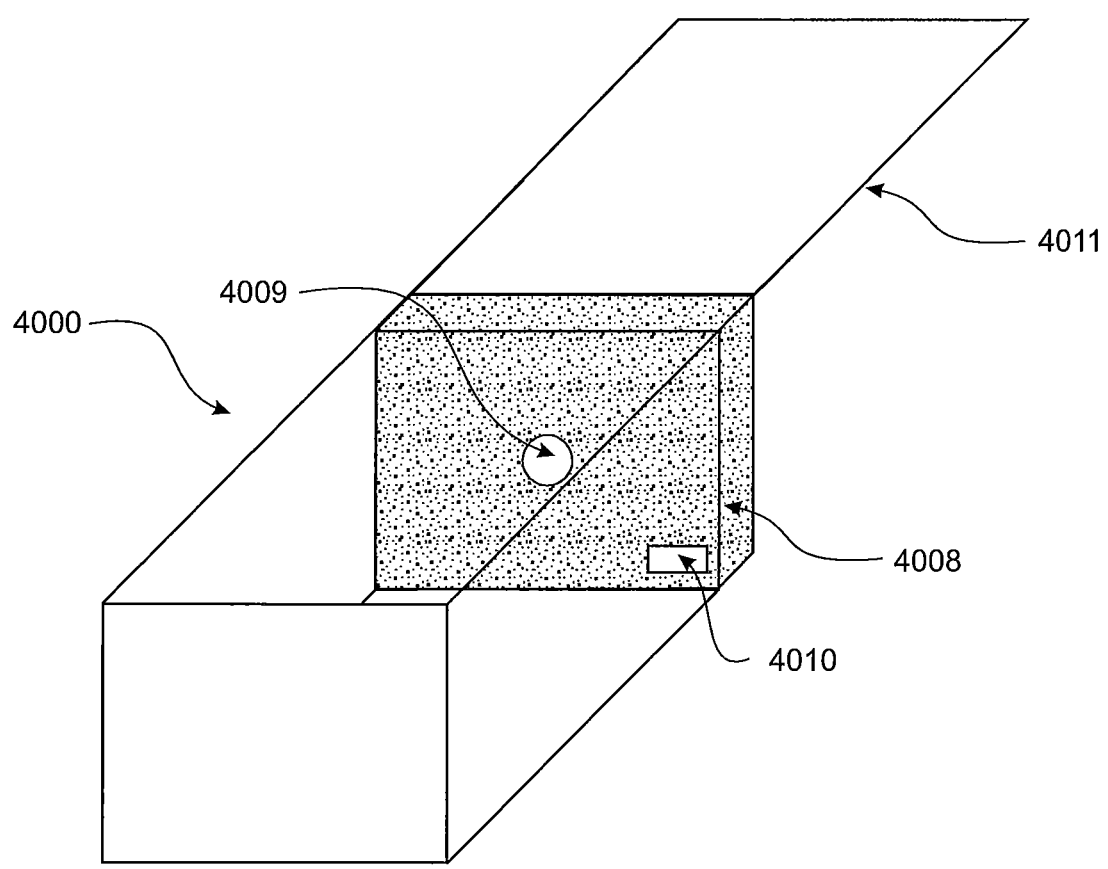
FIG. 17 is a schematic perspective view of a fourth preferred embodiment bag for managing water that leaks or spills out of a humidification chamber of a CPAP unit.

With reference to FIG. 17, a further preferred embodiment bag is shown. Unless described as otherwise below, the features and functioning of the bag should be considered the same as described for the first embodiment above, and like reference numerals indicate like parts with the addition of 3000. In the fourth embodiment, the bag 4000 may have a rigid insert 4008 on a side of the bag that can help to keep the humidifier 201 in the correct position to avoid water spills. The insert 4008 may comprise a connector 4009 that engages with an outlet of the humidifier. The insert 4008 may also have a connector 4010 that engages with a unit inlet, for example a gas inlet. The connector(s) may lead to an internal water reservoir or water retaining material within the insert that can store water spilled from the inlet and/or outlet such that the water may be reused. If a water retaining material is used, it may be a sponge, or other hydrophilic material. Alternatively the connectors may simply prevent any leakage from the inlet and/or outlet. FIG. 17 shows the bag having a lid 4011, however, the general shape of the bag may not have a lid, but have a central zipper, similar to the earlier described embodiments of the bag.

The preferred embodiment bags 1000, 2000, 3000 have each been described as having an opening closed by a zipper 1003, 2003, 3003. Alternatively, the opening may be closed by other suitable mechanisms, such as complementary hook and loop fasteners, domes, buttons, or ties, for example.

Each of the bags 1000, 2000, 3000 described above may prevent accidental spills from the humidifier of the CPAP unit from disrupting the internal electronics of the CPAP unit. Each of the bags is aesthetically appealing and is preferable packaged with the CPAP unit.

Each of the bags 1000, 2000, 3000 described above may be used with a number of humidification devices or integrated flow generation units.

The preferred embodiment bags 1000, 2000, 3000 have been described as having a specified number of layers. In alternative embodiments, the body of the bag may be formed from four or more layers of breathable material.

Any one of the bags described above may be reinforced with a frame, inserts, or stitching.

Any one or more features from any embodiment may be combined with any one or more features from any one or more other embodiments.

Although the present invention has been described in terms of a certain embodiment, other embodiments apparent to those of ordinary skill in the art also are within the scope of this invention. Thus, various changes and modifications may be made without departing from the spirit and scope of the invention. For instance, various components may be repositioned as desired. Moreover, not all of the features, aspects and advantages are necessarily required to practice the present invention. Accordingly, the scope of the present invention is intended to be defined only by the claims that follow.

What is claimed is:

1. A control system comprising:
a respiratory device having a first housing, the respiratory device further including a near fields communications (NFC) chip having a local memory configured to store diagnostic information and one or more of:
patient data relating to one or more patients,
product information including component data relating to one or more components of or for use with the respiratory device, or
other information related to the respiratory device; and
a mobile computing device having a second housing that is separate from the first housing, the mobile computing device configured to receive data from or transmit data to the respiratory device through at least one communications network, the mobile computing device comprising one or more sensors and a user interface configured to control at least one operation parameter of the respiratory device based on data from the one or more sensors,
wherein the mobile computing device or another computer is configured to wirelessly transmit data to the NFC chip, through an NFC connection between the mobile computing device or the other computer and the respiratory device, to update the patient data or the component data stored in the local memory of the NFC chip of the respiratory device when the respiratory device is turned off, and wherein the mobile computing device or the other computing device is configured to facilitate fault finding by identifying fault information leading to a fault of the respiratory device by interrogating the local memory of NFC chip to access the diagnostic information, and the mobile computing device is configured to determine a fault in the respiratory device by processing the diagnostic information while the respiratory device is off.

2. A control system as claimed in claim 1, wherein the mobile computing device is configured to, in response to receiving input from a patient or other user via the user interface, change the at least one operation parameter of the respiratory device.

3. A control system as claimed in claim 1, wherein the user interface comprises at least one user interface element for conveying information to a patient or other user, or for receiving input from a patient or other user to control the at least one operation parameter of the respiratory device using the mobile computing device.

4. A control system as claimed in claim 3, wherein the at least one user interface element comprises one or more of:
a blower element for a patient or other user to adjust a speed of, or turn on or off, a blower of the respiratory device;
a humidity setting element for a patient or other user to view or adjust a humidity setting of the respiratory device;
a wakefulness element for a patient or other user to turn on or off an operation of the mobile computing device or respiratory device that comprises changing the at least one operation parameter of the respiratory device in response to a change in a wakefulness of the patient;
a ramp element for a patient or other user to turn on or off an operation of the mobile computing device or respiratory device that comprises a ramping of a pressure or flow of gas propelled by the respiratory device, or for a patient or other user to change a ramp time of the respiratory device; or
a data element for a patient or other user to view information about the respiratory device, one or more operation parameters of the respiratory device, sensor data from one or more sensors, or information corresponding to sensor data from one or more sensors.

5. A control system as claimed in claim 3, wherein the user interface comprises a graphical user interface.

6. A control system as claimed in claim 1, wherein the mobile computing device is configured to communicate through the at least one communications network with, or wherein the one or more sensors comprise, one or more of:
at least one environment sensor configured to generate data representing a condition of an environment about the mobile computing device or the respiratory device;
at least one patient sensor configured to generate data representing a condition of the patient; or
at least one respiratory device sensor configured to generate data representing an operating condition of the respiratory device.

7. A control system as claimed in claim 6, wherein the at least one environment sensor comprises one or more of: a temperature sensor; a humidity sensor; an atmospheric pressure sensor; a light sensor; or a smoke sensor.

8. A control system as claimed in claim 6, wherein the at least one patient sensor comprises one or more of: an accelerometer; an image sensor; or a sound sensor.

9. A control system as claimed in claim 6, wherein the at least one respiratory device sensor comprises one or more sensors for generating data representing an operating condition of one or more of: a humidifier; a breathing conduit; a patient interface; or a blower.

10. A control system as claimed in claim 1, wherein the mobile computing device is configured to perform at least one of the following:
present, via the user interface, information corresponding to data obtained from the one or more sensors to a patient or other user;
transmit a signal to automatically change, based on data generated by the one or more sensors, the at least one operation parameter of the respiratory device; or
prompt, via the user interface, a patient or other user, based on data generated by the one or more sensors, to change the at least one operation parameter of the respiratory device.

11. A control system as claimed in claim 1, wherein the mobile computing device is configured to, based on data generated by the one or more sensors, indicate an adverse operating condition of the respiratory device, or an adverse condition of an environment about the mobile computing device or the respiratory device, to a patient or other user.

12. A control system as claimed in claim 1, wherein the mobile computing device is configured to, in response to determining a change in wakefulness,
transmit a signal to at least one other electrical device or appliance to change an operation parameter of the at least one other electrical device or appliance; or
transmit a signal to a patient indicator device for waking the patient to trigger the patient indicator device.

13. A control system as claimed in claim 1, wherein the at least one operation parameter of the respiratory device comprises one or more of: a treatment pressure; a treatment flow rate, a blower motor speed, a heater plate power or temperature, a heated breathing tube power, a humidification level, a time setting, an alarm setting, or a threshold for responding to a mask leak.

14. A control system as claimed in claim 1, wherein the mobile computing device comprises at least one of: a laptop computer; a tablet computer; a personal digital assistant (PDA); a cellular phone; or a wearable computing device.

15. A control system as claimed in claim 1, wherein the respiratory device comprises a continuous positive airway pressure (CPAP) device.

16. A control system as claimed in claim 1, comprising:
at least one component of or for use with the respiratory device; and
a wirelessly interrogatable chip integrated into or located on the at least one component, and having local memory configured to store information relating to the at least one component;
wherein the mobile computing device or another computing device is configured to wirelessly interrogate the chip to retrieve information about the at least one component; and
the mobile computing device or other computing device is configured to transmit data corresponding to the information retrieved from the chip to the respiratory device to update component data stored in the memory of the respiratory device.

17. A control system as claimed in claim 1, wherein the NFC chip of the respiratory device comprises a microprocessor.

18. A control system as claimed in claim 17, wherein the microprocessor of the NFC chip is configured to interrogate the local memory of the NFC chip and update settings of the respiratory device based on the updated patient data or component data when the respiratory device is turned on.

19. A control system as claimed in claim 17, wherein the local memory of the NFC chip is configured to store product information, and the mobile computing device is configured to retrieve the product information from the respiratory device via the NFC connection.

20. A control system as claimed in claim 19, wherein the mobile computing device is configured to transmit updated product information onto the respiratory device via the NFC connection and the local memory of the NFC chip of the respiratory device is configured to store the updated product information.

21. A control system as claimed in claim 1, wherein the mobile computing device is configured to establish and authenticate a further wireless connection using the NFC connection between the mobile device and the respiratory device.

22. A control system as claimed in claim 1, wherein the respiratory device configured to apply update settings of the respiratory device for the updated patient data or the component data, wherein the update settings comprise one or more update settings of pressure, flow, or information about other components.

* * * * *